(12) United States Patent
Miller et al.

(10) Patent No.: US 9,422,266 B2
(45) Date of Patent: Aug. 23, 2016

(54) SUBSTITUTED CYCLOPROPYL COMPOUNDS, COMPOSITIONS CONTAINING SUCH COMPOUNDS AND METHODS OF TREATMENT

(71) Applicant: Merck Sharp & Dohme Corp., Rahway, NJ (US)

(72) Inventors: Michael W. Miller, Scotch Plains, NJ (US); Andrew W. Stamford, Chatham Township, NJ (US); Kallol Basu, Hillsborough, NJ (US); Scott Edmondson, Clark, NJ (US); Zhiqiang Guo, Morganville, NJ (US); William B. Geiss, Albany, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 74 days.

(21) Appl. No.: 14/347,268

(22) PCT Filed: Sep. 24, 2012

(86) PCT No.: PCT/US2012/056792
§ 371 (c)(1),
(2) Date: Mar. 26, 2014

(87) PCT Pub. No.: WO2013/048916
PCT Pub. Date: Apr. 4, 2013

(65) Prior Publication Data
US 2014/0256699 A1    Sep. 11, 2014

Related U.S. Application Data

(60) Provisional application No. 61/541,467, filed on Sep. 30, 2011.

(51) Int. Cl.
*C07D 401/12* (2006.01)
*C07D 401/14* (2006.01)
*C07D 211/96* (2006.01)

(52) U.S. Cl.
CPC ............ *C07D 401/12* (2013.01); *C07D 211/96* (2013.01); *C07D 401/14* (2013.01)

(58) Field of Classification Search
CPC .................................................. C07D 401/12
See application file for complete search history.

(56) References Cited

U.S. PATENT DOCUMENTS

| | | |
|---|---|---|
| 6,054,587 A | 4/2000 | Reddy et al. |
| 6,110,903 A | 8/2000 | Kasibhatla et al. |
| 6,284,748 B1 | 9/2001 | Dang et al. |
| 6,399,782 B1 | 6/2002 | Kasibhatla et al. |
| 6,489,476 B1 | 12/2002 | Dang et al. |
| 6,699,871 B2 | 3/2004 | Edmondson et al. |
| 6,730,690 B2 | 5/2004 | Olson et al. |
| 2009/0270409 A1 | 10/2009 | Alper et al. |
| 2010/0022591 A1 | 1/2010 | Bertram et al. |
| 2010/0286112 A1 | 11/2010 | Barba et al. |
| 2011/0028501 A1 | 2/2011 | Wood et al. |
| 2011/0212939 A1 | 9/2011 | Bertram et al. |
| 2012/0053180 A1 | 3/2012 | Kang et al. |
| 2012/0142706 A1 | 6/2012 | Wood et al. |

FOREIGN PATENT DOCUMENTS

| | | |
|---|---|---|
| WO | 98/04528 A2 | 2/1998 |
| WO | 99/01423 A1 | 1/1999 |
| WO | 00/39088 A1 | 7/2000 |
| WO | 00/69810 A1 | 11/2000 |
| WO | 02/08188 A1 | 1/2002 |
| WO | 02/060388 A2 | 8/2002 |
| WO | 03/104207 A2 | 12/2003 |
| WO | 2004/019869 A2 | 3/2004 |
| WO | 2004/020408 A1 | 3/2004 |
| WO | 2004/020409 A1 | 3/2004 |
| WO | 2004/058741 A1 | 7/2004 |
| WO | 2004/066963 A2 | 8/2004 |
| WO | 2006/067531 A1 | 6/2006 |
| WO | 2006/067532 A1 | 6/2006 |
| WO | 2007/003962 A2 | 1/2007 |
| WO | 2007/003964 A1 | 1/2007 |
| WO | 2009/011836 A1 | 1/2009 |
| WO | 2009/034388 A1 | 3/2009 |
| WO | 2009/042053 A2 | 4/2009 |

(Continued)

OTHER PUBLICATIONS

Bays "Pharmacotherapy for dyslipidaemia—current therapies and future agents." Expert Opinion in Pharmacotherapy 2003, 11, 1901-38.*

(Continued)

*Primary Examiner* — David K O Dell
(74) *Attorney, Agent, or Firm* — Anna L. Cocuzzo; Catherine D. Fitch

(57) ABSTRACT

Substituted cyclopropyl compounds of the formula I and the pharmaceutically acceptable salts thereof are disclosed as useful for treating or preventing type 2 diabetes and similar conditions. The compounds are useful as agonists of the g-protein coupled receptor GPR-119. Pharmaceutical compositions and methods of treatment are also included. Another aspect of the invention that is of interest relates to compounds of formula 1a.

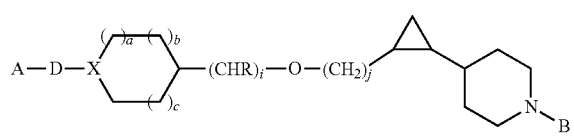

13 Claims, No Drawings

(56) References Cited

FOREIGN PATENT DOCUMENTS

| WO | 2009/129036 A1 | 10/2009 |
| --- | --- | --- |
| WO | 2009/000087 A1 | 12/2009 |
| WO | 2010/004343 A1 | 1/2010 |
| WO | 2010/004344 A1 | 1/2010 |
| WO | 2010/004346 A1 | 1/2010 |
| WO | 2010/004347 A1 | 1/2010 |
| WO | 2010/004348 A1 | 1/2010 |
| WO | 2010/146605 A1 | 12/2010 |
| WO | 2011/008663 A2 | 1/2011 |
| WO | 2011/019538 A1 | 2/2011 |
| WO | 2011/113947 A1 | 9/2011 |
| WO | 2011/127051 A1 | 10/2011 |
| WO | 2012/138845 A1 | 10/2012 |
| WO | 2012/173917 A1 | 12/2012 |
| WO | 2013/048916 A1 | 4/2013 |
| WO | 2013/062838 A1 | 5/2013 |
| WO | 2013/074388 A1 | 5/2013 |
| WO | 2013/122821 A1 | 8/2013 |
| WO | 2014/025379 A1 | 4/2014 |

OTHER PUBLICATIONS

Konstantinos Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.*

Ritter "G Protein-Coupled Receptor 119 (GPR119) Agonists for the Treatment of Diabetes: Recent Progress and Prevailing Challenges" Journal of Medicinal Chemistry, Ahead of Print, 2015.*

Charette, et al., Enantioselective Cyclpropanation of Allylic Alcohols with Dioxaborolane Ligands: Scope and Synthetic Applications, vol. 120, pp. 11943-11952 (1998).

Charette, et al., Stability, Reactivity, Solution, and Solid-State Structure of Halomethylzinc Alkoxides, vol. 123, pp. 12160-12167 (2001).

Costanzi, et al., "On the applicability of GPCR Homology Models . . ." J. Med. Chem., vol. 51, pp. 2907-2914 (2008).

Eymery, et al., "The Usefullness of Phosphorus Compounds in Alkyne Synthesis", Synthesis, No. 2, pp. 185-213 (2000).

Lima, et al., "Bioisosterism: A Useful Strategy for Molecular Modification and Drug Design", Current Medicinal Chemistry, vol. 12, pp. 23-49 (2005).

Chaki, et al., "Recent Advances in feeding suppressing agents: potential therapeutic strategy for the treatment of obesity", Expert Opinion Ther. Patents, vol. 11, No. 11, pp. 1677-1692 (2001).

Spanswick, et al., "Emerging antiobesity drugs", Expert Opinion Emerging Drugs, vol. 8, No. 1, pp. 217-237 (2003).

Fernandez-Lopez, et al., "Pharmacological Approaches for the Treatment of Obesity", Drugs, vol. 62, No. 6, pp. 915-944 (2002).

Gadde, et al., "Combination pharmaceutical therapies for obesity", Expert Opin. Pharmacother., vol. 10, No. 6, pp. 921-925 (2009).

Szewczyk, et al., "Design of potent and selective GPR119 agonists for type II diabetes", Bioorganic & Medicinal Chemistry Letters, vol. 21, pp. 2665-2668 (2011).

International Search Report for PCT/US2012/056792, mailed Jan. 25, 2013.

* cited by examiner

SUBSTITUTED CYCLOPROPYL COMPOUNDS, COMPOSITIONS CONTAINING SUCH COMPOUNDS AND METHODS OF TREATMENT

CROSS-REFERENCE TO RELATED APPLICATIONS

This application is a U.S. National Phase application under 35 U.S.C. §371 of PCT/US2012/056792, filed Sep. 24, 2012, which claims priority from U.S. provisional application 61/541,467, filed Sep. 30, 2011.

BACKGROUND OF THE INVENTION

The present invention relates to G-protein coupled receptor agonists. In particular, the present invention is directed to agonists of GPR 119 that are useful for the treatment of diabetes, especially type 2 diabetes, obesity, the metabolic syndrome and related diseases and conditions.

Diabetes is a disease derived from multiple causative factors. It is characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

Obesity is characterized by excessive adiposity relative to body mass. Clinically, obesity is defined by the body mass index [BMI=weight (kg)/height (m)$^2$], corresponding to BMI values≥30. Obesity and being overweight increases the risk of developing conditions such as high blood pressure, type 2 diabetes, heart disease, stroke, osteoarthritis, sleep apnea, gallbladder disease and cancer of the breast, prostate and colon. Higher body weights are also associated with increases in all-cause mortality.

There is renewed focus on pancreatic islet-based insulin secretion that is controlled by glucose-dependent insulin secretion. In this regard, several orphan G-protein coupled receptors (GPCR's) have recently been identified that are preferentially expressed in the β-cell and are implicated in glucose dependent insulin secretion (GDIS). GPR119 is a cell-surface Gs-coupled GPCR that is highly expressed in human (and rodent) islets as well as in insulin-secreting cell lines. Synthetic GPR119 agonists augment the release of insulin from isolated static mouse islets only under conditions of elevated glucose, and improve glucose tolerance in diabetic mice and diet-induced obese (DIO) C57/B6 mice without causing hypoglycemia. GPR119 agonists therefore have the potential to function as anti-hyperglycemic agents that produce weight loss.

SUMMARY OF THE INVENTION

The present invention relates to compounds represented by formula I:

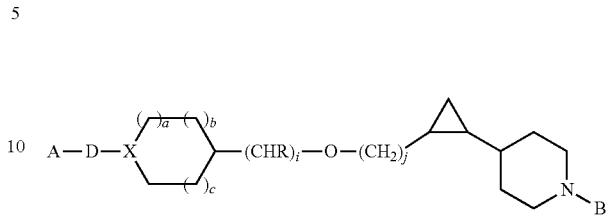

and the pharmaceutically acceptable salts thereof.

DETAILED DESCRIPTION OF THE INVENTION

One aspect of the invention that is of interest relates to a compound represented by formula I:

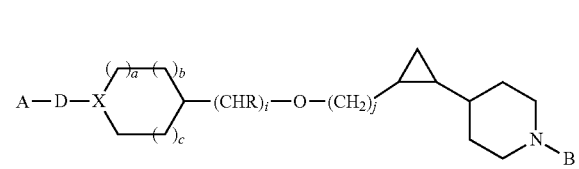

as well as pharmaceutically acceptable salts thereof, wherein:

a, b and c are each 0 or 1, such that one of a, b and c is 1, and the remaining two of a, b and c are either 0 or 1, such that a 4-6 membered ring is defined;

A represents $C_{1-6}$alkyl, halo$C_{1-6}$alkyl, $C_{1-6}$alkoxy $C_{1-6}$alkyl, hydroxy$C_{1-6}$alkyl;

D represents $SO_2$ or C(O);

X represents a C or N atom;

R represents H, $C_{1-6}$alkyl or halo$C_{1-6}$alkyl;

i and j independently represent integers selected from 0, 1 and 2, such that i plus j is 1, 2 or 3;

B represents (a) a 5-6 membered heteroaryl ring 2-3 heteroatoms, 1-3 of which are nitrogen atoms and 0-1 of which is an oxygen or sulfur atom, or (b) $CO_2R^1$, said heteroaryl group (a) being optionally substituted with 1-3 groups selected from $R^2$;

$R^1$ is selected from the group consisting of: $C_{1-6}$alkyl, halo$C_{1-6}$alkyl, phenyl and $C_{1-6}$alkyl-phenyl; and each $R^2$ is independently selected from halo, $C_{1-6}$alkyl, $C_{1-4}$hydroxyalkyl and halo$C_{1-6}$alkyl.

Another aspect of the invention that is of interest relates to compounds of formula Ia:

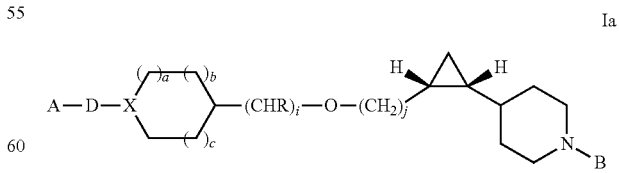

as well as the pharmaceutically acceptable salts thereof.

Another aspect of the invention that is of interest relates to compounds of formula I, as well as the pharmaceutically acceptable salts thereof, wherein X represents a nitrogen atom.

Another aspect of the invention that is of interest relates to compounds of formula I, as well as the pharmaceutically acceptable salts thereof, wherein X is N and the moiety:

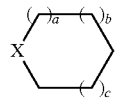

represents a member selected from the group consisting of: piperidine, pyrrolidine and azetedine.

Another aspect of the invention that is of interest relates to compounds of formula I, as well as the pharmaceutically acceptable salts thereof, wherein A represents a member selected from the group consisting of: methyl, ethyl, n-propyl, isopropyl, n-butyl, cyclopropyl and trifluoropropyl.

Another aspect of the invention that is of interest relates to compounds of formula I, as well as the pharmaceutically acceptable salts thereof, wherein R represents H; i represents 0-2 and j represents 0-2, such that the sum of i and j is 1-3.

Another aspect of the invention that is of interest relates to compounds of formula I, as well as the pharmaceutically acceptable salts thereof, wherein B represents

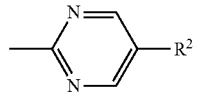

and $R^2$ is selected from the group consisting of halo, which is further selected from chloro and bromo, $C_{1-4}$ alkyl, $C_{1-4}$ hydroxyalkyl and $C_{1-4}$ haloalkyl, in which the halo portion is selected from fluoro, chloro, bromo and iodo.

Another aspect of the invention that is of interest relates to compounds of formula I, as well as the pharmaceutically acceptable salts thereof, wherein B represents $CO_2R^1$, and $R^1$ is selected from the group consisting of $C_{1-6}$alkyl and $C_{1-6}$haloalkyl.

Another aspect of the invention that is of interest relates to compounds of formula I, as well as the pharmaceutically acceptable salts thereof, wherein:

A represents a member selected from the group consisting of: methyl, ethyl, n-propyl, isopropyl, n-butyl, cyclopropyl and trifluoropropyl;

X represents a nitrogen atom;

such that the moiety:

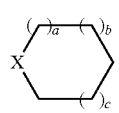

represents a member selected from the group consisting of: piperidine, pyrrolidine and azetedine;

R represents H;

i and j represent 0-1 such that the sum of i and j is 1-3;

B represents

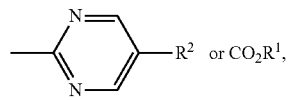

in which $R^1$ is selected from the group consisting of $C_{1-6}$alkyl and halo$C_{1-6}$alkyl and $R^2$ is selected from the group consisting of halo, which is further selected from chloro and bromo, $C_{1-4}$ alkyl, hydroxy$C_{1-4}$alkyl and halo$C_{1-4}$alkyl, in which the halo portion is selected from fluoro, chloro, bromo and iodo.

Another aspect of the invention that is of interest relates to compounds of formula I, as well as the pharmaceutically acceptable salts thereof, selected from the group consisting of:

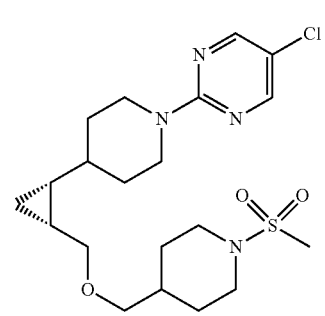

1.1

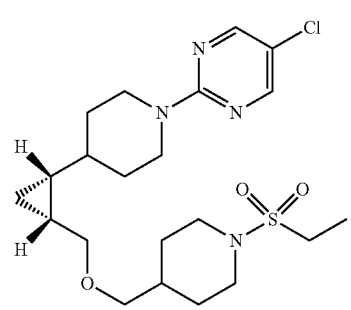

1.2

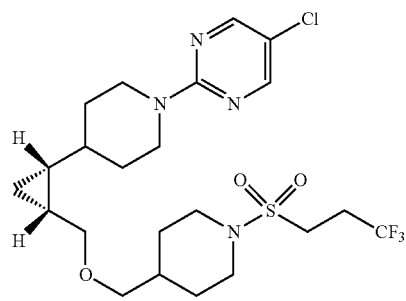

1.3

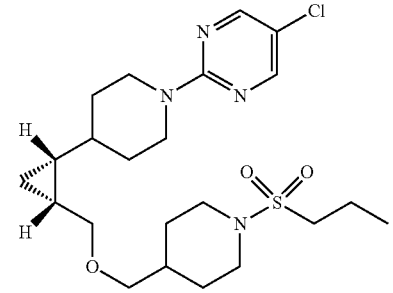

1.4

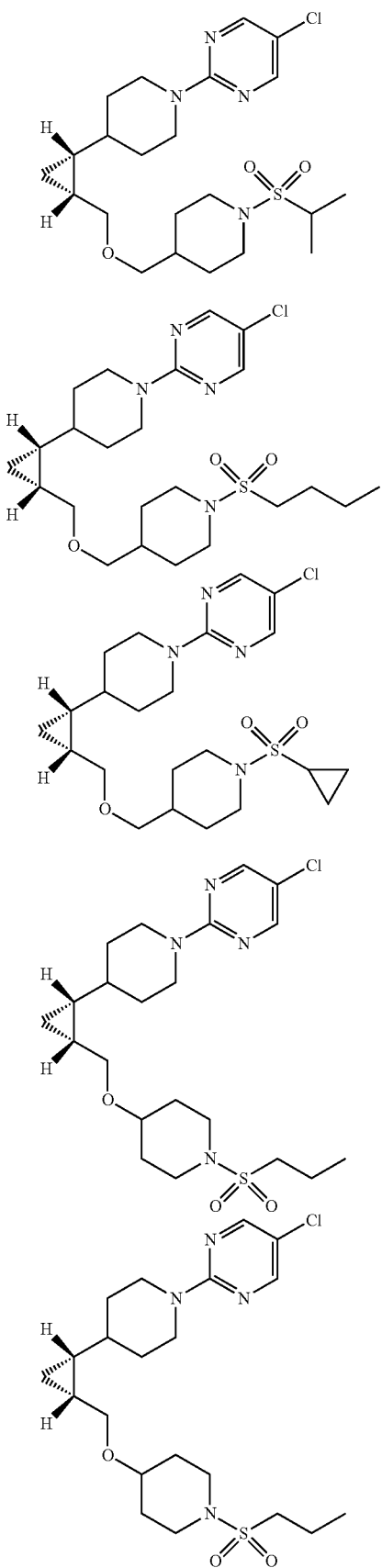
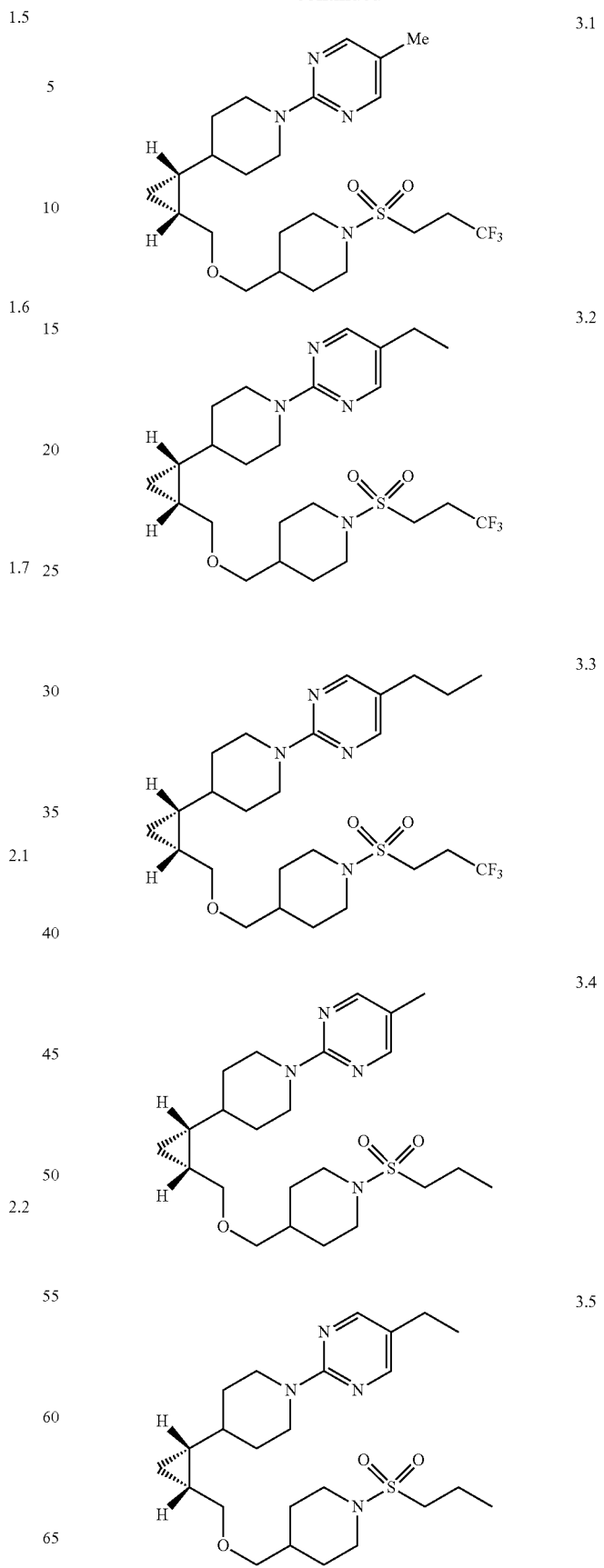

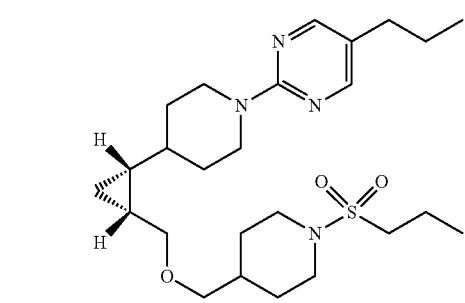
3.6
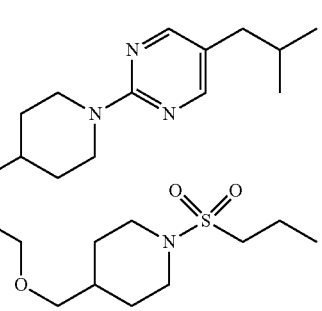
3.7
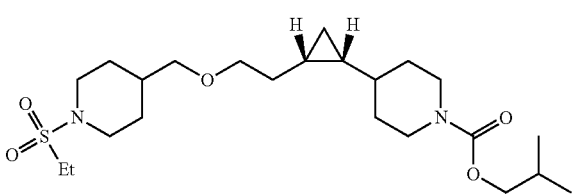
4.1
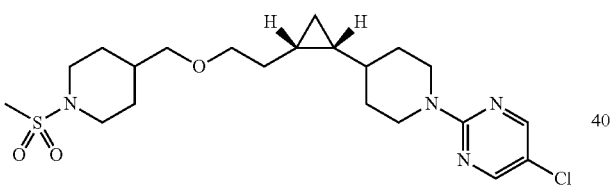
5.2
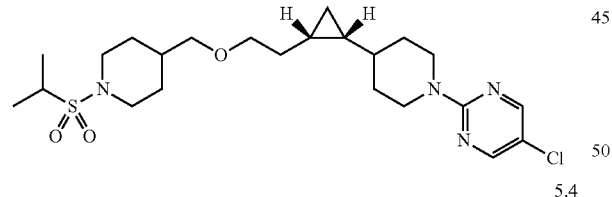
5.3
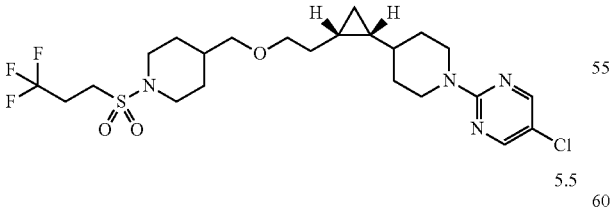
5.4
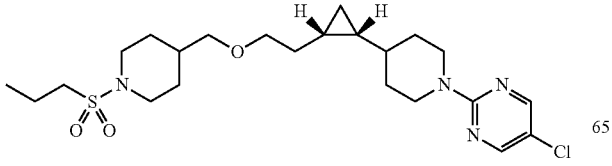
5.5
5.6
5.7
5.8
5.9
5.10

5.11
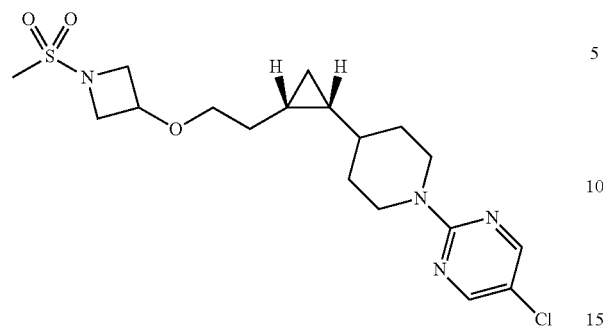
5.12
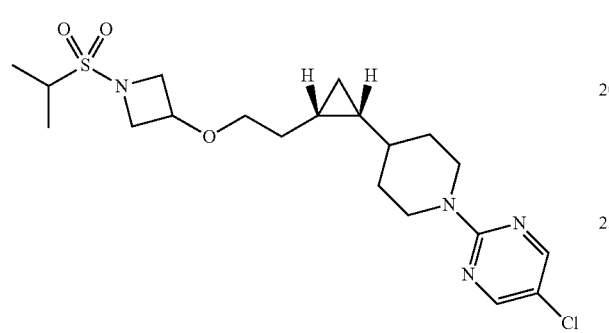
5.13
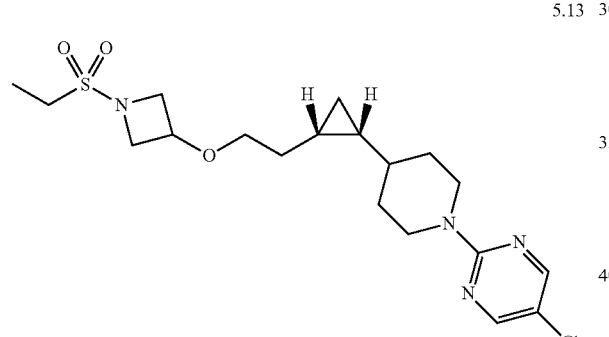
5.14
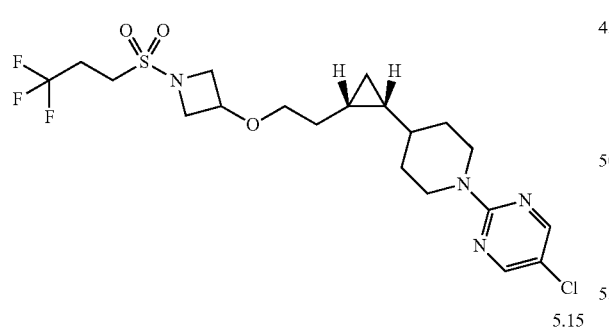
5.15
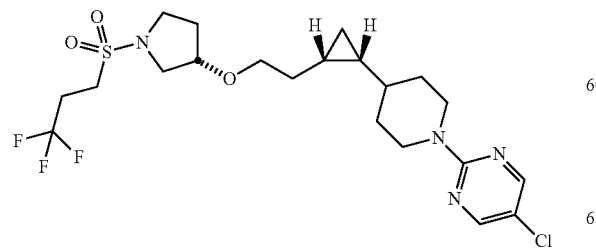
5.16
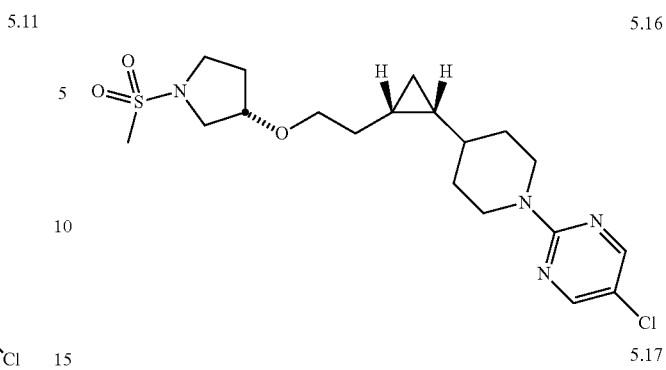
5.17
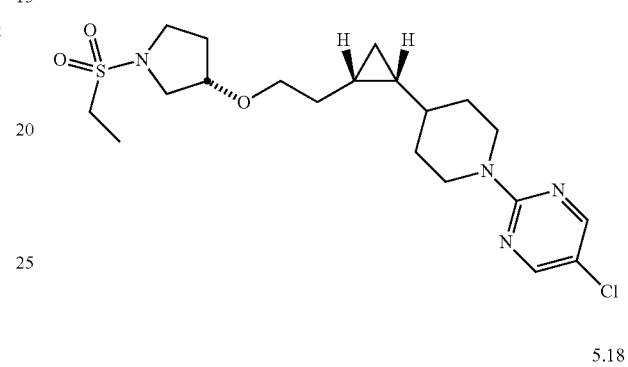
5.18
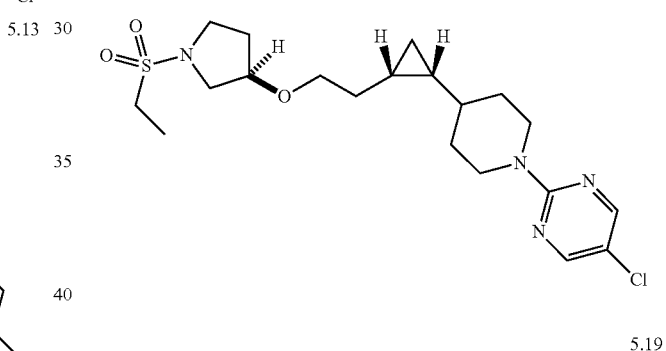
5.19
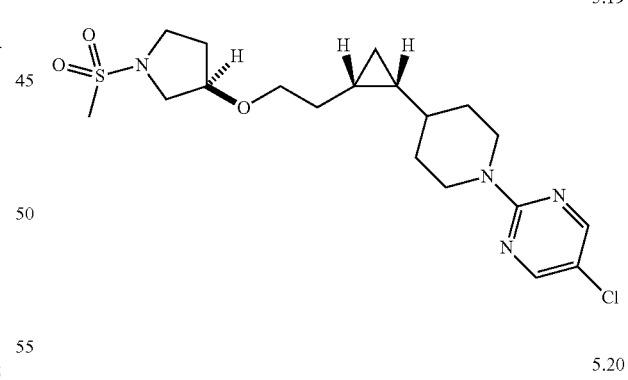
5.20
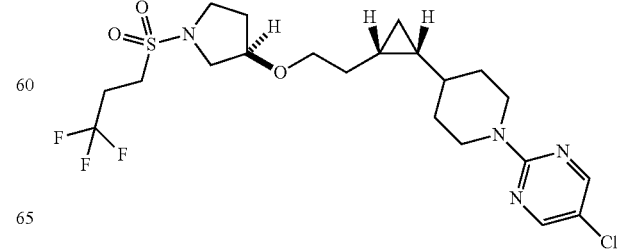

-continued

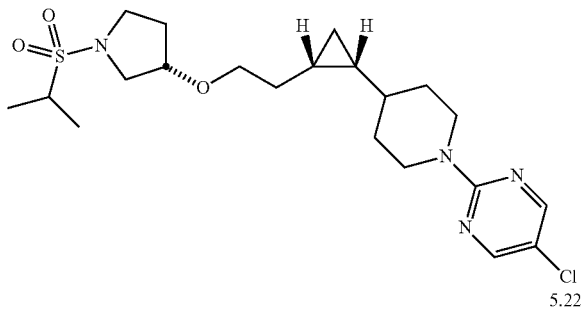

5.21

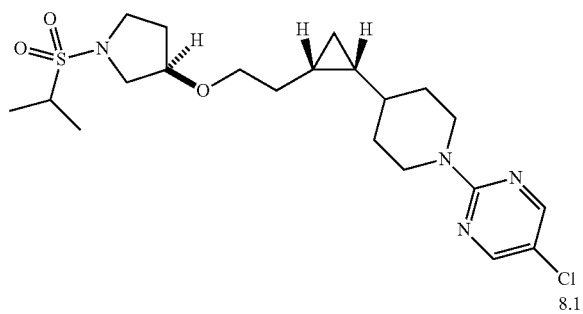

5.22

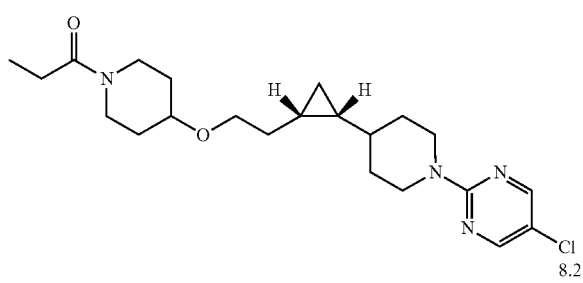

8.1

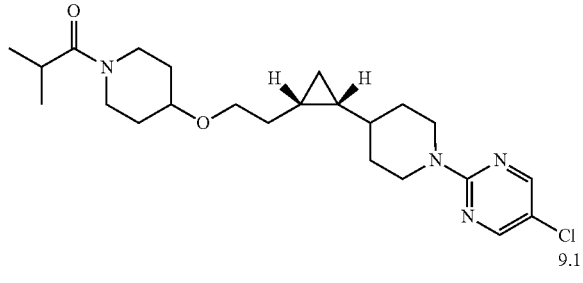

8.2

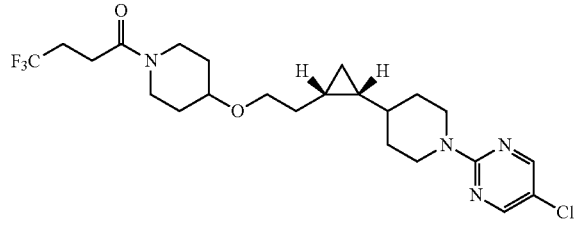

9.1

The invention is described herein in detail using the terms defined below unless otherwise specified.

"Alkyl", as well as other groups having the prefix "alk", such as alkoxy, and the like, means carbon chains which may be linear, branched, or cyclic, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkoxy" refers to an alkyl group linked to oxygen.

"Haloalkoxy" and "haloalkylO" are used interchangeably and refer to halo substituted alkyl groups linked through the oxygen atom. Haloalkoxy include mono-substituted as well as multiple halo substituted alkoxy groups, up to perhalo substituted alkoxy. For example, trifluoromethoxy is included.

"Haloalkyl" include mono-substituted as well as multiple halo substituted alkyl groups, up to perhalo substituted alkyl. For example, trifluoromethyl is included.

"Heteroaryl" (HAR) unless otherwise specified, means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl or pyrrole, isoxazolyl or isoxazole, isothiazolyl or isothiazole, pyrazolyl or pyrazole, pyridyl, oxazolyl or oxazole, oxadiazolyl or oxadiazole, thiadiazolyl or thiadiazole, thiazolyl or thiazole, imidazolyl or imidazole, triazolyl or triazole, tetrazolyl or tetrazole, furyl, triazinyl, thienyl, pyrimidyl, benzisoxazolyl or benzisoxazole, benzoxazolyl or benzoazole, benzothiazolyl or benzothiazole, benzothiadiazolyl or benzothiadiazole, dihydrobenzofuranyl or dihydrobenzofurane, indolinyl or indoline, pyridazinyl or pyridazine, indazolyl or indazole, isoindolyl or isoindole, dihydrobenzothienyl, indolizinyl or indolizine, cinnolinyl or cinnoline, phthalazinyl or phthalazine, quinazolinyl or quinazoline, naphthyridinyl or naphthyridine, carbazolyl or carbazole, benzodioxolyl or benzodioxole, quinoxalinyl or quinoxaline, purinyl or purine, furazanyl or furazane, isobenzylfuranyl or isobenzylfurane, benzimidazolyl or benzimidazole, benzofuranyl or benzofurane, benzothienyl or benzothiene, quinolyl or quinoline, oxo-dihydroqunoline, indolyl or indole, oxindole, isoquinolyl or isoquinoline, dibenzofuranyl or dibenzofurane, and the like. For heterocyclic and heteroaryl groups, rings and ring systems containing from 3-15 atoms are included, forming 1-3 rings.

"Halogen" (Halo) includes fluorine, chlorine, bromine and iodine.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

The individual tautomers of the compounds of the formulas described herein, as well as mixture thereof, are encompassed with compounds of the formulas described herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds of the formulas described herein may be separated into diastereoisomeric pairs of enantiomers by, for example, fractional crystallization from a suitable solvent. The pair of enantiomers thus obtained may be separated into individual stereoisomers by conventional means, for example by the use of an optically active amine or acid as a resolving agent or on a chiral HPLC column.

Alternatively, any enantiomer of a compound of the formulas described herein may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of the structural formulas described herein are also included in the present invention.

Utilities

Compounds of the present invention are potent agonists of the GPR 119 receptor. The compounds of the invention, and pharmaceutically acceptable salts thereof are modulators of the receptor known as GPR 119, and are therefore useful in the treatment of diseases that are modulated by GPR119 ligands and agonists. Many of these diseases are summarized below.

Treatment and prevention of the following diseases and conditions are included in the present invention: Also, the compounds of the invention may be used for the manufacture of a medicament for treating one or more of these diseases or conditions:

(1) noninsulin dependent diabetes mellitus (type 2 diabetes);
(2) hyperglycemia;
(3) the metabolic syndrome;
(4) obesity;
(5) ischemia and myocardial infarction;
(6) neurological disorders such as Alzheimer's disease, schizophrenia, and impaired cognition;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) hyperapobetalipoproteinemia; and
(11) atherosclerosis.

More particularly, the following diseases and conditions can be treated using the compounds of the formulas described herein or a pharmaceutically acceptable salt thereof. The compounds may be used for manufacturing a medicament for the treatment or prevention of one or more of these diseases or conditions:

(1) Type 2 diabetes, and specifically hyperglycemia;
(2) Metabolic syndrome;
(3) Obesity; and
(4) Hypercholesterolemia or dyslipidemia.

Because the compounds are agonists of the GPR119 receptor, the compounds will be useful for lowering glucose, lipids, and insulin resistance in diabetic patients and in non-diabetic patients who have impaired glucose tolerance and/or are in a pre-diabetic condition. The compounds are useful to ameliorate hyperinsulinemia, which often occurs in diabetic or pre-diabetic patients, by modulating the swings in the level of serum glucose that often occurs in these patients. The compounds are useful for treating or reducing insulin resistance. The compounds are useful for treating or preventing gestational diabetes.

The compounds, compositions, and medicaments as described herein are useful for reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

By keeping hyperglycemia under control, the compounds are useful to delay or for preventing vascular restenosis and diabetic retinopathy.

The compounds of this invention are useful in improving or restoring β-cell function, so that they may be useful in treating type 1 diabetes or in delaying or preventing a patient with type 2 diabetes from needing insulin therapy.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds are useful in treating neurological disorders such as Alzheimer's disease, multiple sclerosis, and schizophrenia.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of the formulas described herein or a pharmaceutically acceptable salt thereof. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, pitavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib and anacetrapib), niacin, bile acid sequestrants, microsomal triglyceride transport inhibitors, and bile acid reuptake inhibitors. These combination treatments are useful for the treatment or control of conditions selected from the group consisting of hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound having the formulas described herein or a pharmaceutically acceptable salt thereof. The compound may be used alone or advantageously may be administered with an anti-obesity agent, particularly a lipase inhibitor such as orlistat, or a monoamine neurotransmitter uptake inhibitor such as sibutramine, phentermine and the like. The compound may also be used advantageously in combination with CB-1 inverse agonists or antagonists such as rimonabant and taranabant.

Another aspect of the invention that is of interest relates to a method of treating hyperglycemia, diabetes or insulin resistance in a mammalian patient in need of such treatment which comprises administering to said patient a compound in accordance with the formulas described herein or a pharmaceutically acceptable salt thereof in an amount that is effective to treat hyperglycemia, diabetes or insulin resistance.

More particularly, another aspect of the invention that is of interest relates to a method of treating type 2 diabetes in a mammalian patient in need of such treatment comprising administering to the patient a compound in accordance with the formulas described herein or a pharmaceutically acceptable salt thereof in an amount that is effective to treat type 2 diabetes.

Yet another aspect of the invention that is of interest relates to a method of treating non-insulin dependent diabetes mellitus in a mammalian patient in need of such treatment comprising administering to the patient a compound in accordance with the formulas described herein or a pharmaceutically acceptable salt thereof in an amount that is effective to treat non-insulin dependent diabetes mellitus.

Yet another aspect of the invention that is of interest relates to a method of treating obesity in a mammalian patient in need of such treatment comprising administering to said patient a compound in accordance with the formulas described herein or a pharmaceutically acceptable salt thereof in an amount that is effective to treat obesity.

Yet another aspect of the invention that is of interest relates to a method of treating Syndrome X in a mammalian patient in need of such treatment, comprising administering to said patient a compound in accordance with the formulas described herein or a pharmaceutically acceptable salt thereof in an amount that is effective to treat Syndrome X.

Yet another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound in accordance with the formulas described herein or a pharmaceutically acceptable salt thereof in an amount that is effective to treat said lipid disorder.

Yet another aspect of the invention that is of interest relates to a method of treating atherosclerosis in a mammalian patient in need of such treatment, comprising administering to said patient a compound in accordance with a compound in accordance with the formulas described herein or a pharmaceutically acceptable salt thereof in an amount that is effective to treat atherosclerosis.

Yet another aspect of the invention that is of interest relates to a method of delaying the onset of the aforementioned conditions where insulin resistance is a component, comprising the step of administering to the patient a compound in accordance with the formulas described herein or a pharmaceutically acceptable salt thereof in an amount that is effective to delay the onset of said condition.

Yet another aspect of the invention that is of interest relates to a method of reducing the risk of developing one of the aforementioned conditions and disorders where insulin resistance is a component, comprising the step of administering to the patient a compound in accordance with the formulas described herein or a pharmaceutically acceptable salt thereof in an amount that is effective to reduce the risk of developing said condition.

Yet another aspect of the invention that is of interest relates to a method of treating a condition selected from the group consisting of (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with the formulas described herein or a pharmaceutically acceptable salt thereof in an amount that is effective to treat said condition, and a compound selected from the group consisting of:

(a) DPP-IV inhibitors;
(b) insulin sensitizers selected from the group consisting of (i) PPAR agonists and (ii) biguanides;
(c) insulin and insulin mimetics;
(d) sulfonylureas and other insulin secretagogues;
(e) α-glucosidase inhibitors;
(f) glucagon receptor antagonists;
(g) GLP-1, GLP-1 mimetics, and GLP-1 receptor agonists;
(h) GIP,GIP mimetics, and GIP receptor agonists;
(i) PACAP, PACAP mimetics, and PACAP receptor 3 agonists;
(j) cholesterol lowering agents selected from the group consisting of
  (i) HMG-CoA reductase inhibitors, (ii) sequestrants, (iii) nicotinyl alcohol, nicotinic acid and salts thereof, (iv) PPARα agonists, (v) PPARα/γdual agonists, (vi) inhibitors of cholesterol absorption, (vii) acyl CoA:cholesterol acyltransferase inhibitors, and (viii) anti-oxidants;
(k) PPARδ agonists;
(l) antiobesity compounds;
(m) ileal bile acid transporter inhibitors;
(n) anti-inflammatory agents excluding glucocorticoids;
(o) protein tyrosine phosphatase-1B (PTP-1B) inhibitors; and
(p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; said compounds being administered to the patient in an amount that is effective to treat said condition.

Yet another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a compound in accordance with the formulas described herein or a pharmaceutically acceptable salt thereof and an HMG-CoA reductase inhibitor, in amounts that are effective to treat said condition.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a compound in accordance with the formulas described herein or a pharmaceutically acceptable salt thereof and an HMG-CoA reductase inhibitor in the form of a statin, said compounds being administered in amounts that are effective for treating said condition. Statins useful in this regard include the group consisting of lovastatin, simvastatin, pravastatin, fluvastatin, atorvastatin, itavastatin, pitavastatin, ZD-4522 and rivastatin.

A method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of the formulas described herein and an HMG-CoA reductase inhibitor.

More particularly, another aspect of the invention that is of interest relates to a method of delaying the onset or reducing the risk of developing atherosclerosis in a human patient in need of such treatment comprising administering to the patient a compound in accordance with the formulas described herein or a pharmaceutically acceptable salt thereof and an HMG-CoA reductase inhibitor in the form of a statin, said compounds being administered in amounts that are effective for treating said condition. Statins useful in this regard include the group consisting of lovastatin, simvastatin, pravastatin, fluvastatin, atorvastatin, itavastatin, pitavastatin, ZD-4522 and rivastatin.

More particularly, another aspect of the invention that is of interest relates to a method of treating, delaying the onset or reducing the risk of developing atherosclerosis in a human patient in need of such treatment comprising administering to the patient a compound in accordance with the formulas described herein or a pharmaceutically acceptable salt thereof and a cholesterol absorption inhibitor, said compounds being administered in amounts that treat, delay the onset, or reduce the risk of developing atherosclerosis.

Even more particularly, another aspect of the invention that is of interest relates to a method of treating, delaying the onset or reducing the risk of developing atherosclerosis in a human patient in need of such treatment comprising administering to the patient a compound in accordance with the formulas described herein or a pharmaceutically acceptable salt thereof and a cholesterol absorption inhibitor, wherein the cholesterol absorption inhibitor is ezetimibe, said compounds being administered in amounts that treat, delay the onset, or reduce the risk of developing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the formulas described herein or a pharmaceutically acceptable salt thereof are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of the formulas described herein are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

Pharmaceutical Compositions

Another aspect of the invention that is of interest is a pharmaceutical composition comprised of a compound of the formulas described herein or a pharmaceutically acceptable salt thereof in combination with a pharmaceutically acceptable carrier. The pharmaceutical compositions of the present invention comprise a compound of the formulas described herein or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art of pharmacy.

In practical use, compounds of the formulas described herein, or the pharmaceutically acceptable salts thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of the formulas described herein or a pharmaceutically acceptable salt thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

Combination Therapy

Compounds of the formulas described herein may be used in combination with other drugs that may also be useful in the treatment or amelioration of the diseases and conditions described herein. Such other drugs may be administered by a route and in an amount commonly used therefore, contemporaneously or sequentially with a compound of the formulas described herein or a pharmaceutically acceptable salt thereof. In the treatment of patients who have type 2 diabetes, insulin resistance, obesity, metabolic syndrome, neurological disorders, and co-morbidities that accompany these diseases, more than one drug is commonly administered. The compounds of this invention may generally be administered to a patient who is already taking one or more other drugs for these conditions.

When a compound of the formulas described herein is used contemporaneously with one or more other drugs, a pharmaceutical composition in unit dosage form containing such other drugs and the compound of the formulas described herein is preferred. However, the combination therapy also includes therapies in which a compound of the formulas described herein and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the formulas described herein.

Examples of other active ingredients that may be administered separately or in the same pharmaceutical composition in combination with a compound of the formulas described herein include, but are not limited to:

(1) dipeptidyl peptidase-IV (DPP-4) inhibitors;

(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), such as those disclosed in WO 02/060388, WO 02/08188, WO 2004/019869, WO 2004/020409, WO 2004/020408, and WO 2004/066963, and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; (iii) protein tyrosine phosphatase-1B (PTP-1B) inhibitors;

(3) insulin or insulin analogs, such as insulin lispro, insulin detemir, insulin glargine, insulin glulisine, and inhalable formulations of each thereof;

(4) leptin and leptin derivatives and agonists;

(5) amylin and amylin analogs, such as pramlintide;

(6) sulfonylurea and non-sulfonylurea insulin secretagogues, such as tolbutamide, glyburide, glipizide, glimepiride, mitiglinide, and meglitinides, such as nateglinide and repaglinide;

(7) α-glucosidase inhibitors (such as acarbose, voglibose and miglitol);

(8) glucagon receptor antagonists, such as those disclosed in WO 98/04528, WO 99/01423, WO 00/39088, and WO 00/69810;

(9) incretin mimetics, such as GLP-1, GLP-1 analogs, derivatives, and mimetics; and GLP-1 receptor agonists, such as exenatide, liraglutide, taspoglutide, AVE0010, CJC-1131, and BIM-51077, including intranasal, transdermal, and once-weekly formulations thereof;

(10) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(11) HDL-raising drugs, such as niacin or a salt thereof and extended-release versions thereof; Tredaptive™, which is a combination of niacin extended-release and the DP-1 antagonist LAROPIPRANT; and nicotinic acid receptor agonists;

(12) antiobesity compounds;

(13) agents intended for use in inflammatory conditions, such as aspirin, non-steroidal anti-inflammatory drugs (NSAIDs), glucocorticoids, and selective cyclooxygenase-2 (COX-2) inhibitors;

(14) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(15) glucokinase activators (GKAs), such as LY2599506;

(16) inhibitors of 11β-hydroxysteroid dehydrogenase type 1, such as those disclosed in U.S. Pat. No. 6,730,690; WO 03/104207; and WO 04/058741;

(17) inhibitors of cholesteryl ester transfer protein (CETP), such as torcetrapib and anacetrapib;

(18) inhibitors of fructose 1,6-bisphosphatase, such as those disclosed in U.S. Pat. Nos. 6,054,587; 6,110,903; 6,284,748; 6,399,782; and 6,489,476;

(19) inhibitors of acetyl CoA carboxylase-1 or 2 (ACC1 or ACC2);

(20) AMP-activated Protein Kinase (AMPK) activators;

(21) agonists of the G-protein-coupled receptors: GPR-109, GPR-119, and GPR-40;

(22) SSTR3 antagonists, such as those disclosed in WO 2009/011836;

(23) neuromedin U receptor agonists, such as those disclosed in WO2009/042053, including, but not limited to, neuromedin S (NMS);

(24) inhibitors of stearoyl-coenzyme A delta-9 desaturase (SCD);

(25) GPR-105 antagonists, such as those disclosed in WO 2009/000087;

(26) inhibitors of glucose uptake, such as sodium-glucose transporter (SGLT) inhibitors and its various isoforms, such as SGLT-1; SGLT-2, such as dapagliflozin and remogliflozin; and SGLT-3;

(27) inhibitors of acyl coenzyme A:diacylglycerol acyltransferase 1 and 2 (DGAT-1 and DGAT-2);

(28) inhibitors of fatty acid synthase;

(29) inhibitors of acetyl-CoA carboxylase-1 and 2 (ACC-1 and ACC-2);

(30) inhibitors of acyl coenzyme A:monoacylglycerol acyltransferase 1 and 2 (MGAT-1 and MGAT-2);

(31) agonists of the TGR5 receptor (also known as GPBAR1, BG37, GPCR19, GPR131, and M-BAR);

(32) ileal bile acid transporter inhibitors;

(33) PACAP, PACAP mimetics, and PACAP receptor 3 agonists;

(34) PPARδ agonists;

(35) protein tyrosine phosphatase-1B (PTP-1B) inhibitors; and

(36) bromocriptine mesylate and rapid-release formulations thereof.

Dipeptidyl peptidase-IV (DPP-4) inhibitors that can be used in combination with compounds of the formulas described herein include, but are not limited to, sitagliptin (disclosed in U.S. Pat. No. 6,699,871), vildagliptin, saxagliptin, alogliptin, denagliptin, carmegliptin, dutogliptin, melogliptin, linagliptin, and pharmaceutically acceptable salts thereof, and fixed-dose combinations of these compounds with metformin hydrochloride, pioglitazone, rosiglitazone, simvastatin, atorvastatin, or a sulfonylurea.

Other dipeptidyl peptidase-IV (DPP-4) inhibitors that can be used in combination with compounds of the formulas described herein include, but are not limited to:

(2R,3S,5R)-5-(1-methyl-4,6-dihydropyrrolo[3,4-c]pyrazol-5-(1H)-yl)-2-(2,4,5-trifluorophenyl)tetrahydro-2H-pyran-3-amine;

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-2-(2,5-difluorophenyl)tetrahydro-5-(4,6-dihydropyrrolo[3,4-c]pyrazol-5(1H)-yl)tetrahydro-2H-pyran-3-amine;

(3R)-4-[(3R)-3-amino-4-(2,4,5-trifluorophenyl)butanoyl]-hexahydro-3-methyl-2H-1,4-diazepin-2-one;

4-[(3R)-3-amino-4-(2,5-difluorophenyl)butanoyl]hexahydro-1-methyl-2H-1,4-diazepin-2-one hydrochloride; and (3R)-4-[(3R)-3-amino-4-(2,4,5-trifluorophenyl)butanoyl]-hexahydro-3-(2,2,2-trifluoroethyl)-2H-1,4-diazepin-2-one; and pharmaceutically acceptable salts thereof.

Antiobesity compounds that can be combined with compounds of the formulas described herein include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $\beta_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); J. A. Fernandez-Lopez, et al., "Pharmacological Approaches for the Treatment of Obesity," *Drugs*, 62: 915-944 (2002); and K. M. Gadde, et al., "Combination pharmaceutical therapies for obesity," *Exp. Opin. Pharmacother.*, 10: 921-925 (2009).

Glucagon receptor antagonists that can be used in combination with the compounds of the formulas described herein include, but are not limited to:
N-[4-((1S)-1-{3-(3,5-dichlorophenyl)-5-[6-(trifluoromethoxy)-2-naphthyl]-1H-pyrazol-1-yl}ethyl)benzoyl]-β-alanine;
N-[4-((1R)-1-{3-(3,5-dichlorophenyl)-5-[6-(trifluoromethoxy)-2-naphthyl]-1H-pyrazol-1-yl}ethyl)benzoyl]-β-alanine;
N-(4-{1-[3-(2,5-dichlorophenyl)-5-(6-methoxy-2-naphthyl)-1H-pyrazol-1-yl]ethyl}benzoyl)-β-alanine;
N-(4-{(1S)-1-[3-(3,5-dichlorophenyl)-5-(6-methoxy-2-naphthyl)-1H-pyrazol-1-yl]ethyl}benzoyl)-β-alanine;
N-(4-{(1S)-1-[(R)-(4-chlorophenyl)(7-fluoro-5-methyl-1H-indol-3-yl)methyl]butyl}benzoyl)-β-alanine; and
N-(4-{(1S)-1-[(4-chlorophenyl)(6-chloro-8-methylquinolin-4-yl)methyl]butyl}benzoyl)-β-alanine; and pharmaceutically acceptable salts thereof.

Inhibitors of stearoyl-coenzyme A delta-9 desaturase (SCD) that can be used in combination with the compounds of the formulas described herein include, but are not limited to:
[5-(5-{4-[2-(trifluoromethyl)phenoxy]piperidin-1-yl}-1,3,4-thiadiazol-2-yl)-2H-tetrazol-2-yl]acetic acid;
(2-{4-[2-(trifluoromethyl)phenoxy]piperidin-1-yl}-2,5-bi-1,3-thiazol-4-yl)acetic acid;
(5-{3-[4-(2-bromo-5-fluorophenoxy)piperidin-1-yl]isoxazol-5-yl}-2H-tetrazol-2-yl)acetic acid;
(3-{3-[4-(2-bromo-5-fluorophenoxy)piperidin-1-yl]-1,2,4-oxadiazol-5-yl}-1H-pyrrol-1-yl)acetic acid;
(5-{5-[4-(2-bromo-5-fluorophenoxy)piperidin-1-yl]pyrazin-2-yl}-2H-tetrazol-2-yl)acetic acid; and
(5-{2-[4-(5-bromo-2-chlorophenoxy)piperidin-1-yl]pyrimidin-5-yl}-2H-tetrazol-2-yl)acetic acid; and pharmaceutically acceptable salts thereof.

Glucokinase activators that can be used in combination with the compounds of the formulas described herein include, but are not limited to:
3-(6-ethanesulfonylpyridin-3-yloxy)-5-(2-hydroxy-1-methyl-ethoxy)-N-(1-methyl-1H-pyrazol-3-yl)benzamide;
5-(2-hydroxy-1-methyl-ethoxy)-3-(6-methanesulfonylpyridin-3-yloxy)-N-(1-methyl-1H-pyrazol-3-yl)benzamide;
5-(1-hydroxymethyl-propoxy)-3-(6-methanesulfonylpyridin-3-yloxy)-N-(1-methyl-1H-pyrazol-3-yl)benzamide;
3-(6-methanesulfonylpyridin-3-yloxy)-5-(1-methoxymethyl-propoxy)-N-(1-methyl-1H-pyrazol-3-yl)benzamide;
5-isopropoxy-3-(6-methanesulfonylpyridin-3-yloxy)-N-(1-methyl-1H-pyrazol-3-yl)benzamide;
5-(2-fluoro-1-fluoromethyl-ethoxy)-3-(6-methanesulfonylpyridin-3-yloxy)-N-(1-methyl-1H-pyrazol-3-yl)benzamide;
3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide;
3-({4-[(1-methylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide;
N-(3-methyl-1,2,4-thiadiazol-5-yl)-6-[(4-methyl-4H-1,2,4-triazol-3-yl)thio]-3-{[4-(2-pyrrolidin-1-ylethoxy)phenyl]thio}pyridine-2-carboxamide; and
3-[(4-{2-[(2R)-2-methylpyrrolidin-1-yl]ethoxy}phenyl)thio-N-(3-methyl-1,2,4-thiadiazol-5-yl)-6-[(4-methyl-4H-1,2,4-triazol-3-yl)thio]pyridine-2-carboxamide; and pharmaceutically acceptable salts thereof.

Agonists of the GPR-119 receptor that can be used in combination with the compounds of the formulas described herein include, but are not limited to:
rac-cis 5-chloro-2-{4-[2-(2-{[5-(methylsulfonyl)pyridin-2-yl]oxy}ethyl)cyclopropyl]piperidin-1-yl}pyrimidine;
5-chloro-2-{4-[(1R,2S)-2-(2-{[5-(methylsulfonyl)pyridin-2-yl]oxy}ethyl)cyclopropyl]piperidin-1-yl}pyrimidine;
rac cis-5-chloro-2-[4-(2-{2-[4-(methylsulfonyl)phenoxy]ethyl}cyclopropyl)piperidin-1-yl]pyrimidine;
5-chloro-2-[4-((1S,2R)-2-{2-[4-(methylsulfonyl)phenoxy]ethyl}cyclopropyl) piperidin-1-yl]pyrimidine;
5-chloro-2-[4-((1R,2S)-2-{2-[4-(methylsulfonyl)phenoxy]ethyl}cyclopropyl) piperidin-1-yl]pyrimidine;
rac cis-5-chloro-2-[4-(2-{2-[3-(methylsulfonyl)phenoxy]ethyl}cyclopropyl)piperidin-1-yl]pyrimidine; and
rac cis-5-chloro-2-[4-(2-{2-[3-(5-methyl-1,3,4-oxadiazol-2-yl)phenoxy]ethyl}cyclopropyl)piperidin-1-yl]pyrimidine; and pharmaceutically acceptable salts thereof.

Selective PPARγ modulators (SPPARγM's) that can be used in combination with the compounds of the formulas described herein include, but are not limited to:
(2S)-2-({6-chloro-3-[6-(4-chlorophenoxy)-2-propylpyridin-3-yl]-1,2-benzisoxazol-5-yl}oxy)propanoic acid;
(2S)-2-({6-chloro-3-[6-(4-fluorophenoxy)-2-propylpyridin-3-yl]-1,2-benzisoxazol-5-yl}oxy)propanoic acid;
(2S)-2-{[6-chloro-3-(6-phenoxy-2-propylpyridin-3-yl)-1,2-benzisoxazol-5-yl]oxy}propanoic acid;
(2R)-2-({6-chloro-3-[6-(4-chlorophenoxy)-2-propylpyridin-3-yl]-1,2-benzisoxazol-5-yl}oxy)propanoic acid;
(2R)-2-{3-[3-(4-methoxy)benzoyl-2-methyl-6-(trifluoromethoxy)-1H-indol-1-yl]phenoxy}butanoic acid;
(2S)-2-{3-[3-(4-methoxy)benzoyl-2-methyl-6-(trifluoromethoxy)-1H-indol-1-yl]phenoxy}butanoic acid;
2-{3-[3-(4-methoxy)benzoyl-2-methyl-6-(trifluoromethoxy)-1H-indol-1-yl]phenoxy}-2-methylpropanoic acid; and
(2R)-2-{3-[3-(4-chloro)benzoyl-2-methyl-6-(trifluoromethoxy)-1H-indol-1-yl]phenoxy}propanoic acid; and pharmaceutically acceptable salts thereof.

Inhibitors of 11β-hydroxysteroid dehydrogenase type 1 that can be used in combination with the compounds of the formulas described herein include, but are not limited to:

3-[1-(4-chlorophenyl)-trans-3-fluorocyclobutyl]-4,5-dicyclopropyl-r-4H-1,2,4-triazole;

3-[1-(4-chlorophenyl)-trans-3-fluorocyclobutyl]-4-cyclopropyl-5-(1-methylcyclopropyl)-r-4H-1,2,4-triazole;

3-[1-(4-chlorophenyl)-trans-3-fluorocyclobutyl]-4-methyl-5-[2-(trifluoromethoxy)phenyl]-r-4H-1,2,4-triazole;

3-[1-(4-chlorophenyl)cyclobutyl]-4-methyl-5-[2-(trifluoromethyl)phenyl]-4H-1,2,4-triazole;

3-{4-[3-(ethylsulfonyl)propyl]bicyclo[2.2.2]oct-1-yl}-4-methyl-5-[2-(trifluoromethyl)phenyl]-4H-1,2,4-triazole;

4-methyl-3-{4-[4-(methylsulfonyl)phenyl]bicyclo[2.2.2]oct-1-yl}-5-[2-(trifluoromethyl)phenyl]-4H-1,2,4-triazole;

3-(4-{4-methyl-5-[2-(trifluoromethyl)phenyl]-4H-1,2,4-triazol-3-yl}bicyclo[2.2.2]oct-1-yl)-5-(3,3,3-trifluoropropyl)-1,2,4-oxadiazole;

3-(4-{4-methyl-5-[2-(trifluoromethyl)phenyl]-4H-1,2,4-triazol-3-yl}bicyclo[2.2.2]oct-1-yl)-5-(3,3,3-trifluoroethyl)-1,2,4-oxadiazole;

5-(3,3-difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

5-(1-fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

2-(1,1-difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole;

2-(3,3-difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole; and 5-(1,1-difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; and pharmaceutically acceptable salts thereof.

Somatostatin subtype receptor 3 (SSTR3) antagonists that can be used in combination with the compounds of the formulas described herein include, but are not limited to:

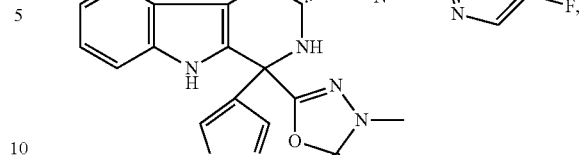

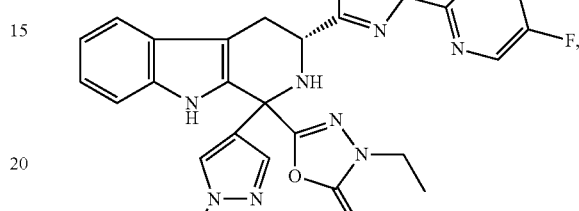

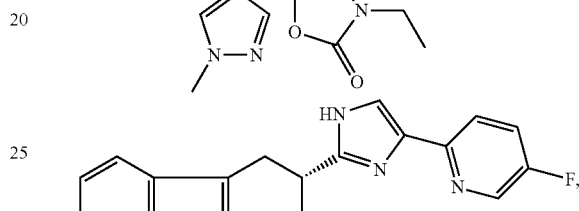

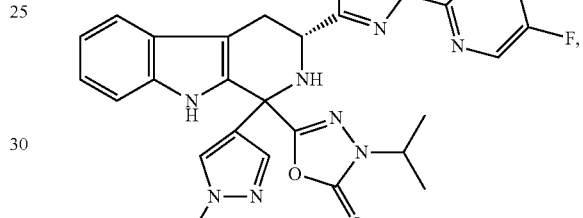

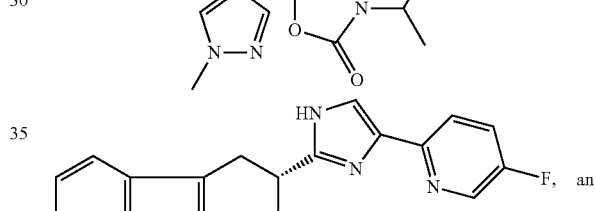

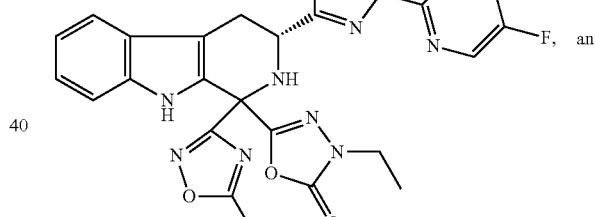

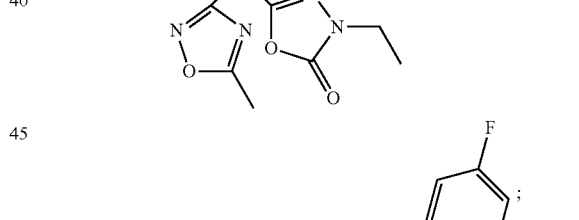

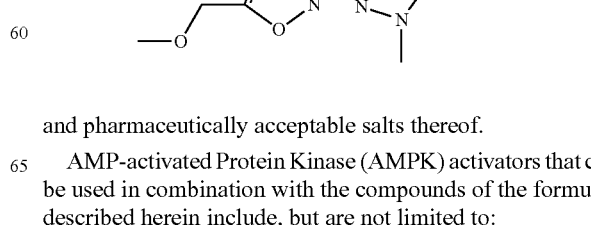

and pharmaceutically acceptable salts thereof.

AMP-activated Protein Kinase (AMPK) activators that can be used in combination with the compounds of the formulas described herein include, but are not limited to:

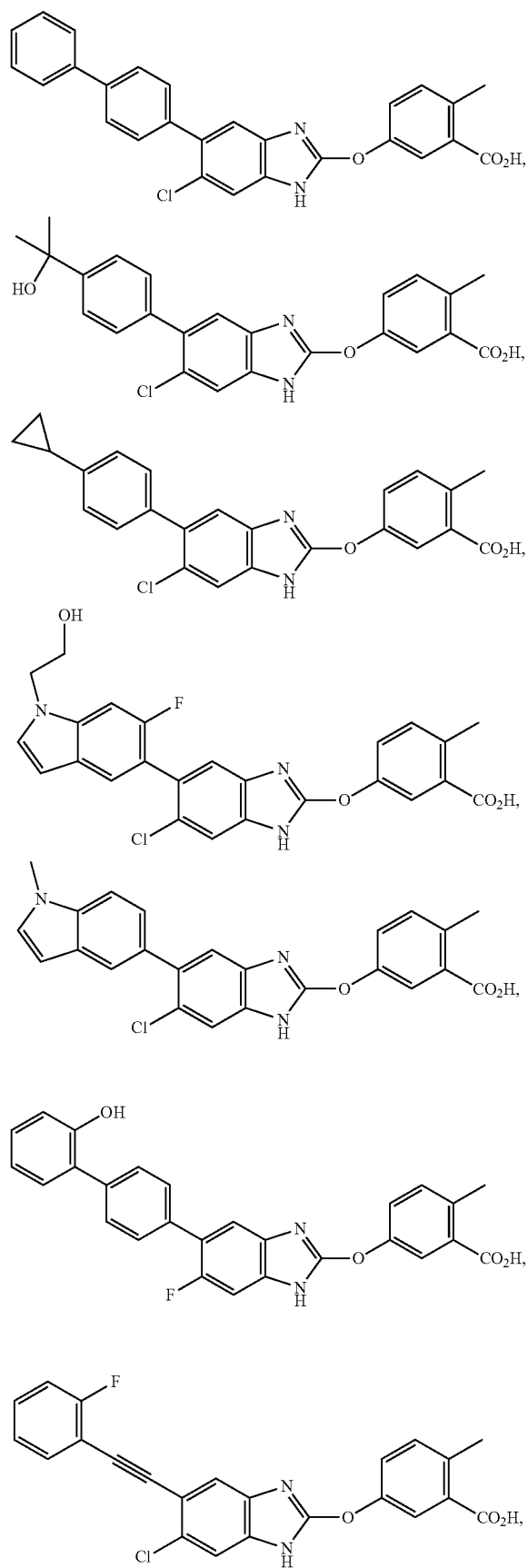
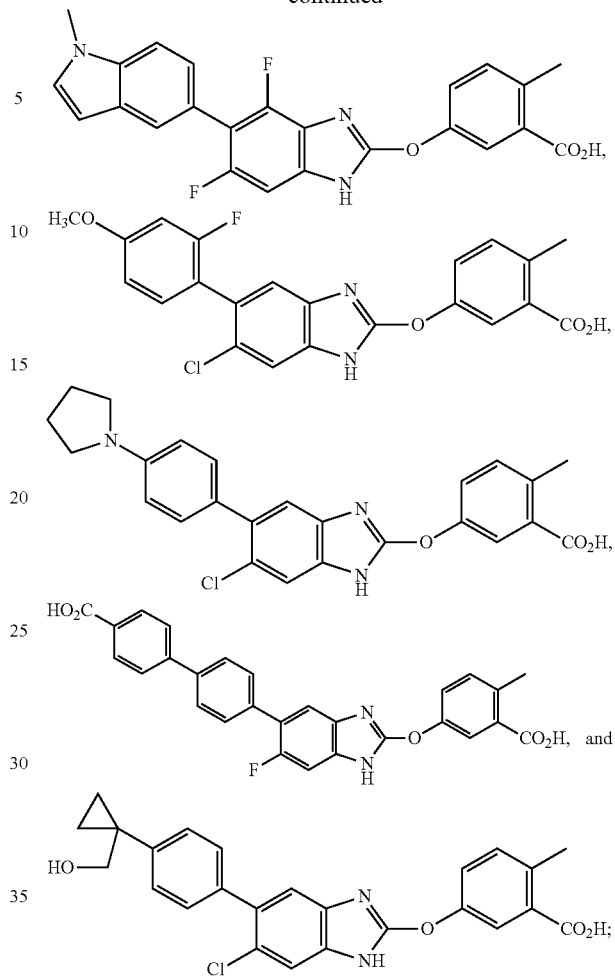

and pharmaceutically acceptable salts thereof.

Inhibitors of acetyl-CoA carboxylase-1 and 2 (ACC-1 and ACC-2) that can be used in combination with the compounds of the formulas described herein include, but are not limited to:

3-{1-[(1-cyclopropyl-4-methoxy-1H-indol-6-yl)carbonyl]-4-oxospiro[chroman-2,4-piperidin]-6-yl}benzoic acid;
5-{1-[(1-cyclopropyl-4-methoxy-1H-indol-6-yl)carbonyl]-4-oxospiro[chroman-2,4-piperidin]-6-yl}nicotinic acid;
1-[(1-cyclopropyl-4-methoxy-1H-indol-6-yl)carbonyl]-6-(1H-tetrazol-5-yl)spiro[chroman-2,4-piperidin]-4-one;
1-[(1-cyclopropyl-4-ethoxy-3-methyl-1H-indol-6-yl)carbonyl]-6-(1H-tetrazol-5-yl)spiro[chroman-2,4-piperidin]-4-one; and
5-{1-[(1-cyclopropyl-4-methoxy-3-methyl-1H-indol-6-yl)carbonyl]-4-oxospiro[chroman-2,4-piperidin]-6-yl}nicotinic acid; and pharmaceutically acceptable salts thereof.

In another aspect of the invention, a pharmaceutical composition is disclosed which comprises one or more of the following agents:

(a) a compound having the structure of the formulas described herein; and
(b) one or more compounds selected from the group consisting of:
(1) dipeptidyl peptidase-IV (DPP-4) inhibitors;
(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; (iii) protein tyrosine phosphatase-1B (PTP-1B) inhibitors;

(3) sulfonylurea and non-sulfonylurea insulin secretagogues, such as tolbutamide, glyburide, glipizide, glimepiride, mitiglinide, and meglitinides, such as nateglinide and repaglinide;

(4) α-glucosidase inhibitors (such as acarbose, voglibose and miglitol);

(5) glucagon receptor antagonists;

(6) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(7) HDL-raising drugs, such as niacin or a salt thereof and extended-release versions thereof; Tredaptive™, which is a combination of niacin extended-release and the DP-1 antagonist LAROPIPRANT; and nicotinic acid receptor agonists;

(8) antiobesity compounds;

(9) agents intended for use in inflammatory conditions, such as aspirin, non-steroidal anti-inflammatory drugs (NSAIDs), glucocorticoids, and selective cyclooxygenase-2 (COX-2) inhibitors;

(10) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(11) glucokinase activators (GKAs), such as LY2599506;

(12) inhibitors of 11β-hydroxysteroid dehydrogenase type 1;

(13) inhibitors of cholesteryl ester transfer protein (CETP), such as torcetrapib and anacetrapib;

(14) inhibitors of fructose 1,6-bisphosphatase;

(15) inhibitors of acetyl CoA carboxylase-1 or 2 (ACC1 or ACC2);

(16) AMP-activated Protein Kinase (AMPK) activators;

(17) agonists of the G-protein-coupled receptors: GPR-109, GPR-119, and GPR-40;

(18) SSTR3 antagonists;

(19) neuromedin U receptor agonists, including, but not limited to, neuromedin S (NMS);

(20) inhibitors of stearoyl-coenzyme A delta-9 desaturase (SCD);

(21) GPR-105 antagonists;

(22) inhibitors of glucose uptake, such as sodium-glucose transporter (SGLT) inhibitors and its various isoforms, such as SGLT-1; SGLT-2, such as dapagliflozin and remogliflozin; and SGLT-3;

(23) inhibitors of acyl coenzyme A:diacylglycerol acyltransferase 1 and 2 (DGAT-1 and DGAT-2);

(24) inhibitors of fatty acid synthase;

(25) inhibitors of acetyl-CoA carboxylase-1 and 2 (ACC-1 and ACC-2);

(26) inhibitors of acyl coenzyme A:monoacylglycerol acyltransferase 1 and 2 (MGAT-1 and MGAT-2);

(27) agonists of the TGR5 receptor (also known as GPBAR1, BG37, GPCR19, GPR131, and M-BAR); and

(28) bromocriptine mesylate and rapid-release formulations thereof; and (c) a pharmaceutically acceptable carrier.

The above combinations include combinations of a compound of the present invention not only with one other active compound, but also with two or more other active compounds. Non-limiting examples include combinations of compounds of the formulas described herein or a pharmaceutically acceptable salt thereof with two or more active compounds selected from biguanides, sulfonylureas, HMG-CoA reductase inhibitors, other PPAR agonists, PTP-1B inhibitors, DPP-4 inhibitors, and anti-obesity compounds.

Another aspect of the invention that is of interest relates to the use of a compound in accordance with the formulas described herein or a pharmaceutically acceptable salt thereof in the manufacture of a medicament for use in treating a disease or condition described herein.

The compounds of the invention can be prepared using the synthetic schemes described herein as well as any of several alternate methods which will be apparent to a chemist skilled in the art. The following abbreviations may be used in the synthetic schemes or Examples:

Ac is acetyl [$CH_3C(O)$—]; $Ac_2O$ is acetic anhydride; AcAc is acetyl acetonoate; AIBN is azobisiobutyronitrile; Ar is Aryl; ArX is an aryl halide; 9-BBN is 9-borabicyclo[3.3.1] nonane; Bn is benzyl; BOc is tert Butyloxycarbonyl; BuTM-DOB is trans 2-butyl-N,N,N,N-tetramethyl-1,3,2-dioxaborolane-4,5-dicarboxamide, as specified R,R or S,S; DBU is diazabicycloundecane; DBAD is di-tert-butylazodicarboxylate; DCM is dichloromethane; DCE is dichloroethane; DIAD is diisopropylazodicarboxylate; DIBAL or DiBAl-His diisobutylaluminum hydride; DMA is dimethylacetamide; DMAP is dimethylaminopyridine; DMF is N,N-dimethylformamide; DMSO is dimethyl sulfoxide; EDAC (or EDC, or EDCI) is 1-ethyl-3-[3-(dimethylamino)propyl]-carbodiimide HCl; $Et_3N$ is triethylamine; Et is ethyl; EtOAc is ethyl acetate; EtOH is ethanol; HATU is 2-(1H-7-azabenzotriazol-1-yl)-1,1,3,3-tetramethyl uronium hexafluorophosphate methanaminium; HCl is hydrochloric acid; Het-X is heterocyclic halide; HOBt is 1-hydroxybenzotriazole; HPLC is high performance liquid chromatography; iPrOAc is isopropyl acetate; LG is leaving group; LRMS is low resolution mass spectrometry; M is molar; mmol is millimole; Me is methyl; MeOH is methanol; MsCl methanesulfonyl chloride; N is normal; NaHMDS is sodium hexamethyldisiliazide; NaOAc is sodium acetate; NaOtBu is sodium tert-butoxide; n-BuLi is n-butyllithium; NBS is N-bromosuccinimide; NMO is N-methylmorpholine N-oxide; NMP is N-methylpyrrolidinone; $Pd(dba)_2$ is tris(dibenzylideneacetone)dipalladium; $PdCl_2(Ph_3P)_2$ is dichlorobis-(triphenylphosphene) palladium; PG Denotes an unspecified protecting group; Ph is phenyl; PhMe is toluene; $PPh_3$ is triphenylphosphine; PMB is para-methoxybenzyl; RT is room temperature; TBAF is tetrabutyl ammonium fluoride; TBS is tert-butyldimethylsilyl; tBu is tert-butyl; TEA is triethylamine; Tf is triflate; TFA is trifluoroacetic acid; THF is tetrahydrofuran; TLC is thin layer chromatography; TMEDA is tetramethylethylenediamine; TMS is trimethylsilyl; TPAP is tetrapropylammonium perruthenate, Ts or TsCl is tosyl or tosyl chloride.

General Schemes

Experimental Section

Scheme 1

Example 1.1

Step 1

To a cold (0° C.), stirred solution of alcohol (5.0 g, 19.58 mmol) in dichloromethane (100 mL) was added trifluoroacetic acid (100 mL) slowly over 10 minutes. After being stirred at 0° C. for 1 h, the mixture was concentrated under vacuum. Residual trifluoroacetic acid was further removed by evaporating twice from dichloromethane followed by drying in vacuum.

The residue was dissolved in DMF (40 ml) followed by the addition of cesium carbonate (35.09 g, 107.69 mmol) and 2,5-dichloropyrimidine (2.92 g, 19.58 mmol). The mixture was stirred at room temperature for 5 h before being quenched with $H_2O$. The aqueous layer was extracted with EtOAc (2×). The combined organic layers were washed with $H_2O$ (2×), brine (1×), dried over anhydrous $MgSO_4$, filtered, and concentrated under vacuum to leave a residue which was purified by column chromatography on silica (elution with 20:1

DCM:MeOH) to afford the desired product as a white solid. LCMS calc: 267.1; obs: 268.1 [M+H]⁺.

Step 2

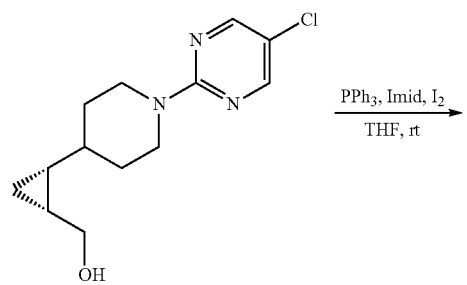

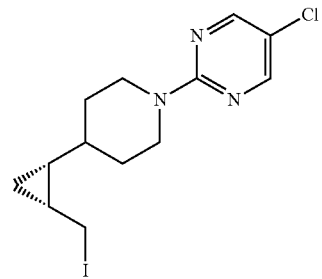

To a stirred solution of alcohol (2.0 g, 7.47 mmol), PPh₃ (2.55 g, 9.71 mmol) and imidazole (1.02 g, 14.94 mmol) in THF (35 mL) was added I₂ (2.28 g, 8.96 mmol) in one portion. The resulting dark mixture was stirred at room temperature for 2 h before being quenched with an aqueous solution of Na₂S₂O₃ followed by the addition of DCM. The organic layer was separated and the aqueous layer was extracted with DCM (2×). The combined organic layers were dried over Mg₂SO₄, filtered and concentrated to leave a residue which was purified by column chromatography on silica (elution with 10:1 hexane:ethyl acetate) to afford the iodide as a colorless gum. LCMS calc: 377.0; obs: 378.2 [M+H]⁺.

Step 3

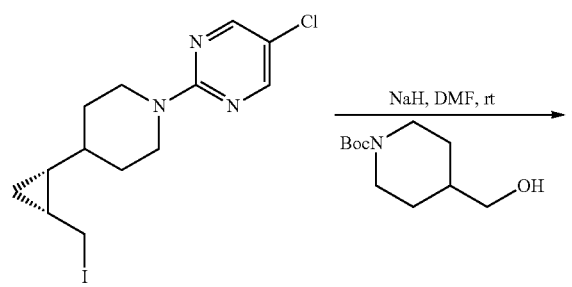

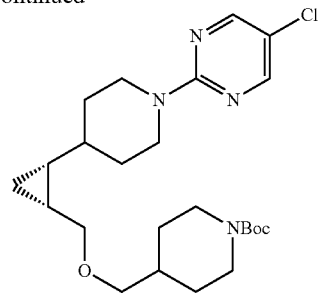

To a cold (0° C.), stirred solution of 1-Boc-4-hydroxymethylpiperidine (258 mg, 1.2 mmol) in DMF (3.6 mmol) was added NaH (52 mg of 60% in oil, 1.3 mmol) in one portion. The mixture was stirred at 0° C. for 15 min followed by stirring at room temperature for 30 min. The mixture was then cooled to 0° C. and a solution of iodide (378 mg, 1.0 mmol) in DMF (3 mL) was added via syringe dropwise. After being stirred at room temperature for 15 h, the reaction was quenched with H₂O. The mixture was extracted with EtOAc (2×). The combined organic layers were washed with H₂O (2×), brine (1×), dried over anhydrous MgSO₄, filtered and concentrated to leave a residue which was purified by column chromatography on silica (elution with 30:1 DCM:MeOH) to afford the desired ether as a colorless gum. LCMS calc: 464.3; obs: 465.3 [M+H]⁺.

Step 4

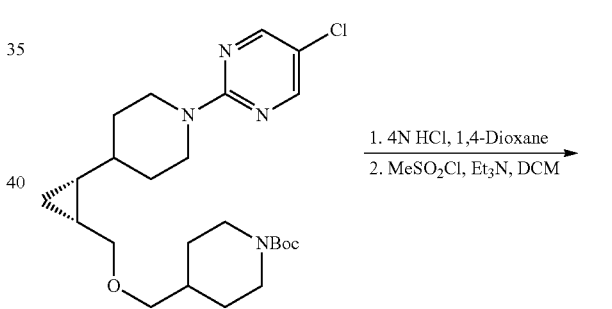

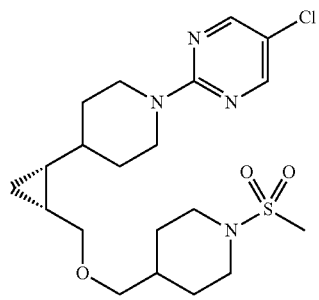

Example 1.1

A mixture of the ether (0.32 g, 0.68 mmol) from Step 3 and 4N HCl in 1,4-dioxane (1.7 mL, 6.8 mmol) was stirred in 1,4-dioxane (3.5 mL) at room temperature for 15 h. The mixture was concentrated and hydrochloride salt was used directly in the next step without further purification.

To a stirred solution of the hydrochloride salt (60 mg, 0.149 mmol) and triethylamine (75 mg, 0.745 mmol) in dichloromethane (2 mL) was added methanesulfonyl chloride (26 mg, 0.224 mmol) at room temperature. After being stirred at room temperature for 5 h, the reaction was concentrated and purified by Preparative TLC (elution with 40:1 DCM:MeOH) to afford Example 1.1 as a colorless gum. LCMS calc: 442.2; obs: 443.2 [M+H]+.

TABLE 1.1

The following examples were prepared in a manner similar to the procedure outlined in Scheme 1 using the appropriate reagents.

| Example | Reagent | Structure |
|---|---|---|
| 1.2 | EtSO2Cl | 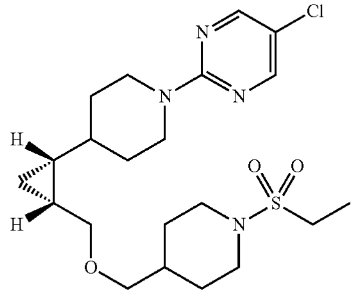 [SMILES: CCS(=O)(=O)N1CCC(COC[C@@H]2C[C@@H]2C2CCN(c3ncc(Cl)cn3)CC2)CC1] |
| 1.3 | CF2CH2CH2SO2Cl | 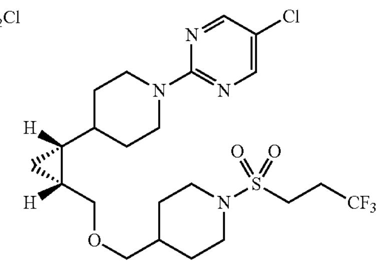 |
| 1.4 | n-PRSO2Cl | 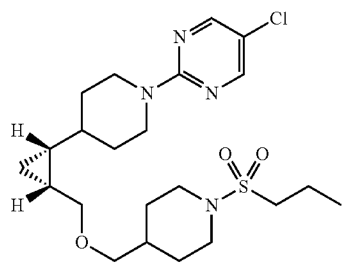 [SMILES: CCCS(=O)(=O)N1CCC(COC[C@@H]2C[C@@H]2C2CCN(c3ncc(Cl)cn3)CC2)CC1] |
| 1.5 | i-PRSO2Cl | 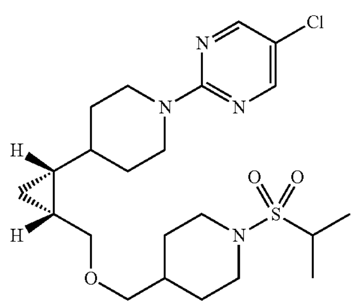 [SMILES: CC(C)S(=O)(=O)N1CCC(COC[C@@H]2C[C@@H]2C2CCN(c3ncc(Cl)cn3)CC2)CC1] |
| 1.6 | n-BuSO2Cl | 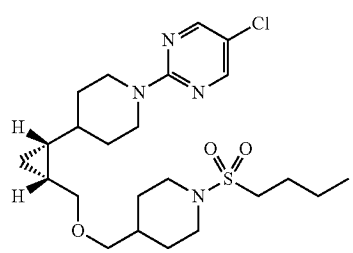 [SMILES: CCCCS(=O)(=O)N1CCC(COC[C@@H]2C[C@@H]2C2CCN(c3ncc(Cl)cn3)CC2)CC1] |

TABLE 1.1-continued

The following examples were prepared in a manner similar to the procedure outlined in Scheme 1 using the appropriate reagents.

| Example | Reagent | Structure |
|---|---|---|
| 1.7 | c-PRSO2Cl | 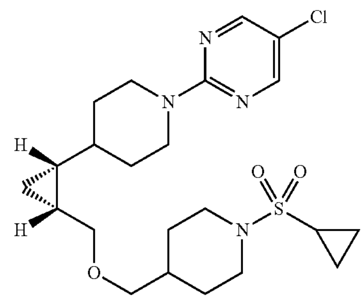 [SMILES: O=S(=O)(C1CC1)N1CCC(COC[C@@H]2C[C@@H]2C2CCN(c3ncc(Cl)cn3)CC2)CC1] |

Scheme 2

NaH, DMF, rt

1. TFA, DCM
2. n-BuSO2Cl, Et3N
CH2Cl2

Step 2

Example 2.1

Step 1

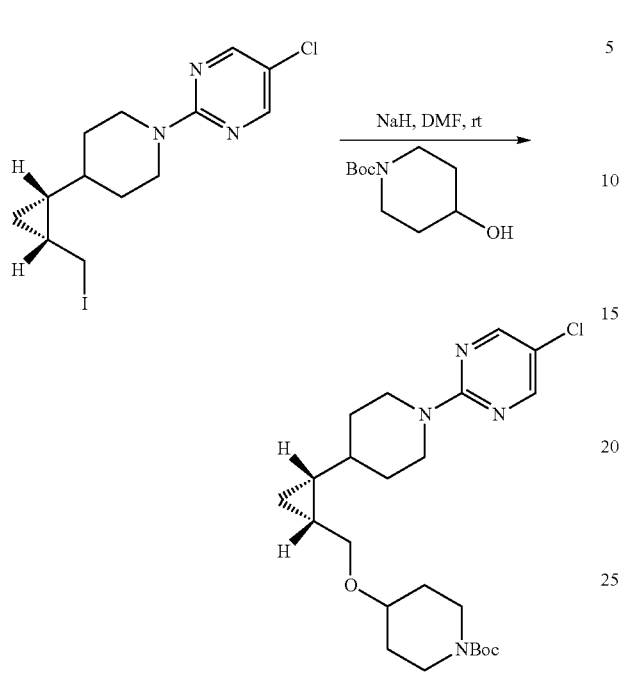

To a cold (0° C.), stirred solution of 1-Boc-4-hydroxypiperidine (1.13 g, 5.60 mmol) in DMF (7 mL) was added NaH (0.22 g of 60% in oil, 5.60 mmol) in portion. The mixture was stirred at 0° C. for 15 min then was stirred at room temperature for 30 min. The mixture was then cooled to 0° C. and a solution of iodide (1.41 g, 3.73 mmol) in DMF (7 mL) was added via syringe dropwise. After being stirred at room temperature for 15 h, the reaction was quenched with water. The aqueous layer was extracted with EtOAc (2×). The combined organic layers were washed with $H_2O$ (2×), brine (1×), dried over anhydrous $MgSO_4$, filtered and concentrated to leave a residue which was purified by column chromatography on silica (elution with 30:1 DCM:MeOH) to afford the desired ether as a colorless gum. LCMS calc: 450.2; obs: $[M+H]^+$.

Step 2

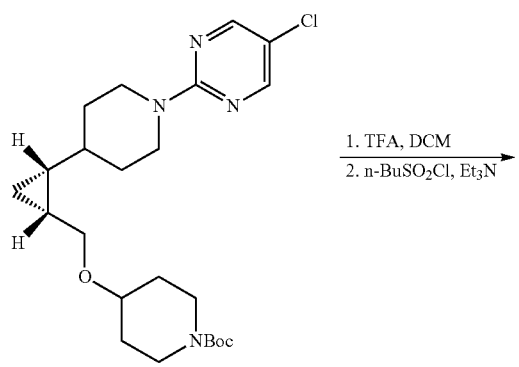

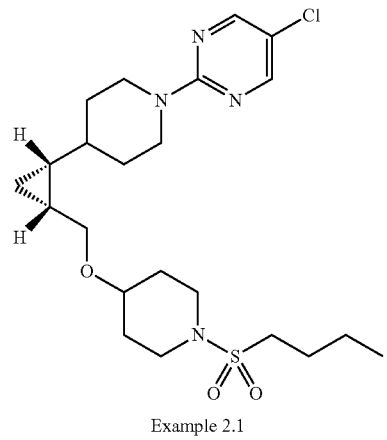

Example 2.1

To a cold (0° C.), stirred solution of ether (1.18 g, 2.61 mmol) in dichloromethane (8 mL) was added trifluoroacetic acid (8 mL) dropwise. After being stirred at 0° C. for 1 h, the mixture was concentrated under vacuum. Residual trifluoroacetic acid was removed by dissolving the residue in dichloromethane and concentrating, followed by drying under vacuum.

To a stirred solution of the TFA salt (50 mg, 0.112 mmol) and triethylamine (56 mg, 0.558 mmol) in dichloromethane (1 mL) was added butanesulfonyl chloride (35 mg, 0.223 mmol) at room temperature. After being stirred at room temperature for 5 h, the reaction was concentrated and purified by Preparative TLC (elution with 40:1 DCM:MeOH) to afford Example 2.1 as a colorless gum. LCMS calc: 470.2; obs: 471.3 $[M+H]^+$.

TABLE 2.1

The following example was prepared by a method similar to that outlined in Scheme 2 using the appropriate reagents.

| Example | Reagent | Structure |
|---------|---------|-----------|
| 2.2 | n-PrSO$_2$Cl | 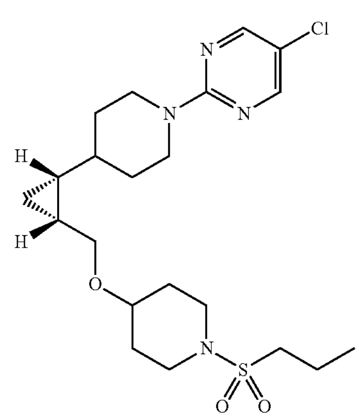 [SMILES: CCCS(=O)(=O)N1CCC(OC[C@@H]2C[C@@H]2C2CCN(c3ncc(Cl)cn3)CC2)CC1] |

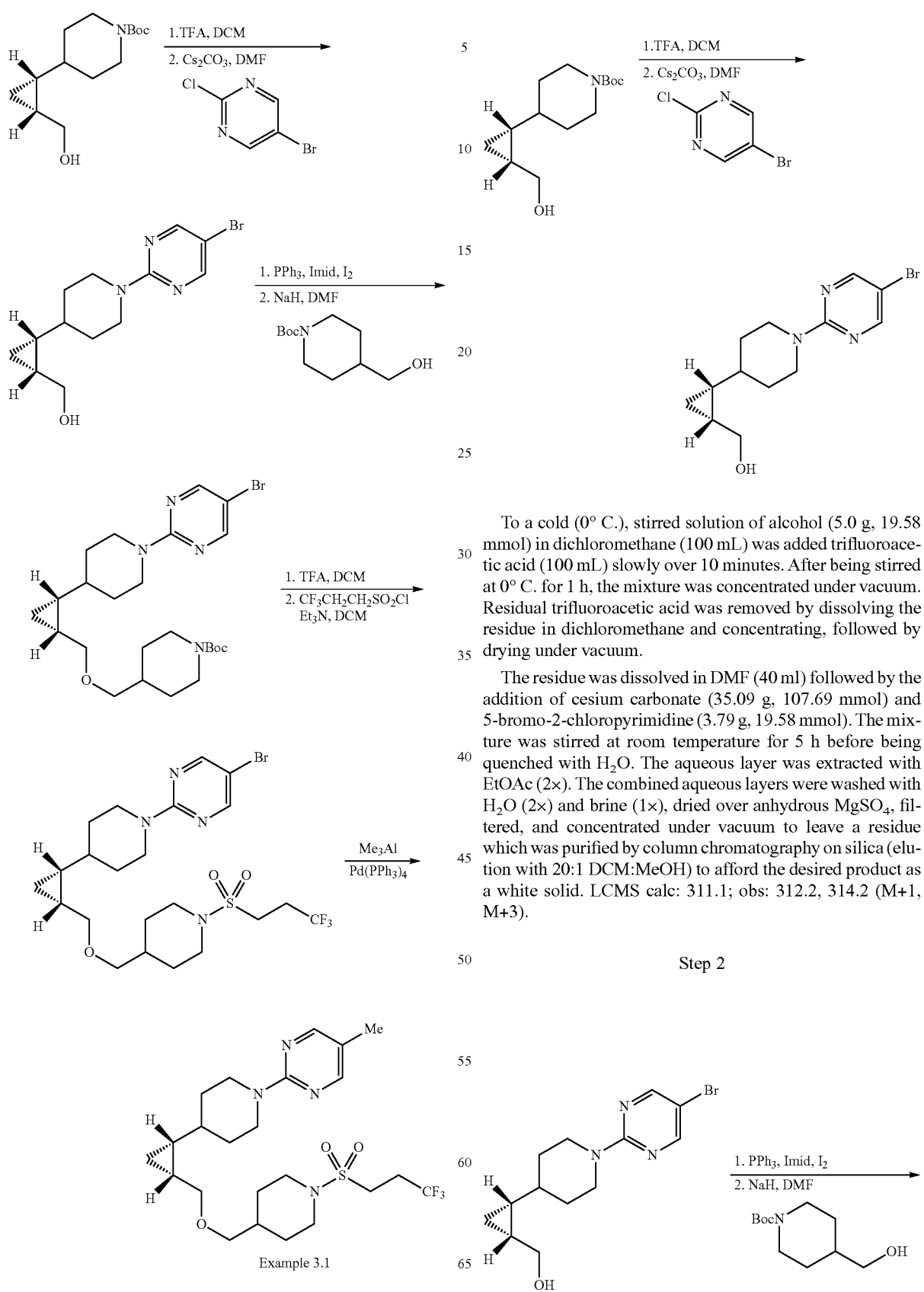

Step 1

To a cold (0° C.), stirred solution of alcohol (5.0 g, 19.58 mmol) in dichloromethane (100 mL) was added trifluoroacetic acid (100 mL) slowly over 10 minutes. After being stirred at 0° C. for 1 h, the mixture was concentrated under vacuum. Residual trifluoroacetic acid was removed by dissolving the residue in dichloromethane and concentrating, followed by drying under vacuum.

The residue was dissolved in DMF (40 ml) followed by the addition of cesium carbonate (35.09 g, 107.69 mmol) and 5-bromo-2-chloropyrimidine (3.79 g, 19.58 mmol). The mixture was stirred at room temperature for 5 h before being quenched with $H_2O$. The aqueous layer was extracted with EtOAc (2×). The combined aqueous layers were washed with $H_2O$ (2×) and brine (1×), dried over anhydrous $MgSO_4$, filtered, and concentrated under vacuum to leave a residue which was purified by column chromatography on silica (elution with 20:1 DCM:MeOH) to afford the desired product as a white solid. LCMS calc: 311.1; obs: 312.2, 314.2 (M+1, M+3).

Step 2

-continued

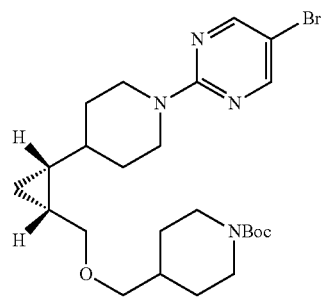

To a stirred solution of alcohol (0.73 g, 2.3 mmol), PPh₃ (0.80 g, 3.04 mmol) and imidazole (0.32 g, 4.68 mmol) in THF (10 mL) was added I₂ (0.89 g, 3.51 mmol) in one portion. The resulting dark mixture was stirred at room temperature for 2 h before being quenched with an aqueous solution of Na₂S₂O₃ followed by the addition of DCM. The organic layer was separated and the aqueous layer was extracted with DCM (2×). The combined organic layers were dried over Mg₂SO₄, filtered and concentrated to leave a residue which was filtered through a pad of silica (elution with 10:1 hexane:ethyl acetate) to afford the iodide which was used in the next step without further characterization.

To a cold (0° C.), stirred solution of 1-Boc-4-hydroxymethylpiperidine (0.61 g, 1.2 mmol) in DMF (5 mmol) was added NaH (0.13 g of 60% in oil, 3.32 mmol) in one portion. The mixture was stirred at 0° C. for 15 min followed by stirring at room temperature for 30 min. The mixture was then cooled to 0° C. and a solution of iodide (1.0 g, 1.0 mmol) in DMF (5 mL) was added via syringe dropwise. After being stirred at room temperature for 15 h, the reaction was quenched with H₂O. The mixture was extracted with EtOAc (2×). The combined organic layers were washed with H₂O (2×), brine (1×), dried over Mg₂SO₄, filtered and concentrated to leave a residue which was purified by column chromatography on silica (elution with 30:1 DCM:MeOH) to afford the desired ether as a colorless gum. LCMS calc: 508.2; obs: 509.3[M+H]⁺.

Step 3

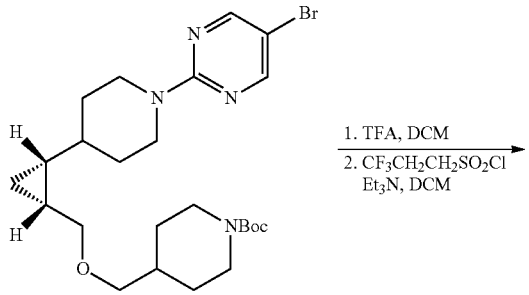

-continued

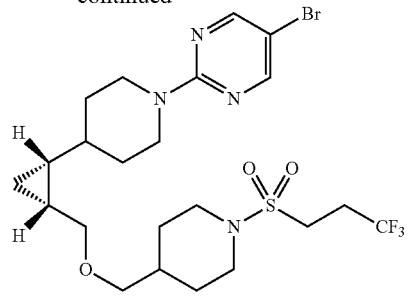

To a cold (0° C.), stirred solution of the ether prepared in Step 2 (0.52 g, 1.02 mmol) in dichloromethane (7 mL) was added trifluoroacetic acid (7 mL) slowly over 10 minutes. After being stirred at 0° C. for 2 h, the mixture was concentrated under vacuum. Residual trifluoroacetic acid was removed by dissolving the residue in dichloromethane and concentrating, followed by drying under vacuum. To a stirred solution of the TFA salt (0.35 g, 0.7 mmol) and triethylamine (0.35 g, 3.5 mmol) in dichloromethane (4 mL) was added 3,3,3-trifluoropropane-1-sulfonyl chloride (0.20 g, 1.05 mmol) at room temperature. After being stirred at room temperature for 5 h, the reaction was quenched with H₂O. The organic layer was separated and the aqueous layer was extracted with DCM (2×). The combined organic layers were dried over anhydrous MgSO₄, filtered, and concentrated under vacuum to leave a residue which was purified by column chromatography on silica (elution with 5:1 hexane:ethyl acetate) to afford the desired sulfonamide as a colorless solid. LCMS calc: 568.1; obs: 569.3 (M+1), 571.3 (M+3).

Step 4

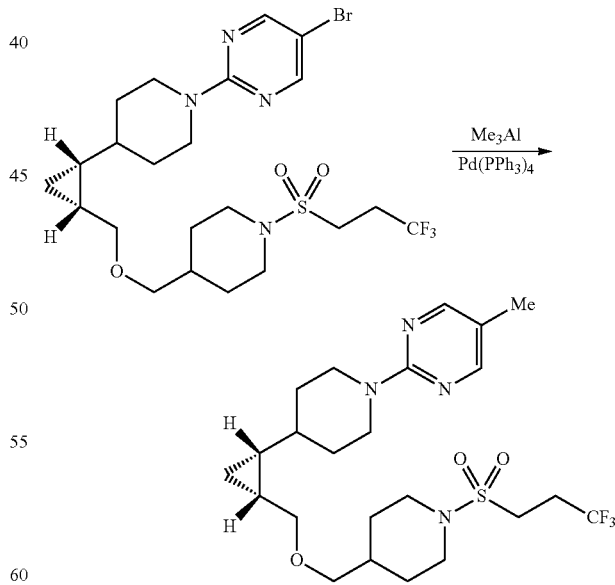

Example 3.1

A mixture of the aryl bromide (40 mg, 0.070 mmol), Pd(PPh₃)₄ (4.1 mg, 0.0035 mmol) and Me₃Al (0.11 mL of 2.0 M solution in toluene, 0.211 mmol) in THF (1.5 mL) was heated at 70° C. for 15 h. The reaction was then cooled to room temperature and carefully quenched with an aqueous solution of K-Na-tartrate. After being stirred at room temperature for 1 h the mixture was extracted with DCM (3×). The combined organic layers were dried over anhydrous MgSO₄, filtered, and concentrated under vacuum to leave a residue which was purified by Preparative TLC on silica (elution with 2:1 hexane:ethyl acetate) to afford Example 3.1. LCMS calc: 504.2; obs: 505.3 (M+1).

TABLE 3.1

The following examples were prepared in a manner similar to that outlined in Scheme 3 using the appropriate reagents.

| Example | Sulfonyl Chloride | (alkyl)₃Al | Structure |
|---|---|---|---|
| 3.2 | 3,3,3-trifluoropropanesulfonyl chloride | Et₃Al | 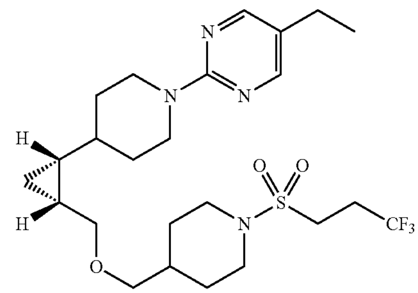 [SMILES: CCc1cnc(N2CCC([C@H]3C[C@H]3COCC3CCN(S(=O)(=O)CCC(F)(F)F)CC3)CC2)nc1] |
| 3.3 | 3,3,3-trifluoropropanesulfonyl chloride | n-PR₃Al | 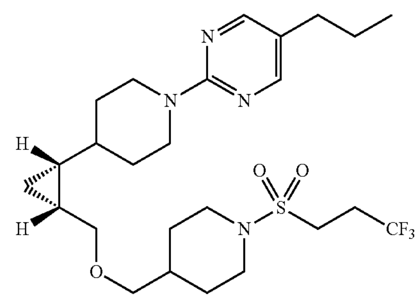 [SMILES: CCCc1cnc(N2CCC([C@H]3C[C@H]3COCC3CCN(S(=O)(=O)CCC(F)(F)F)CC3)CC2)nc1] |
| 3.4 | n-PRSO₂Cl | Me₃Al | 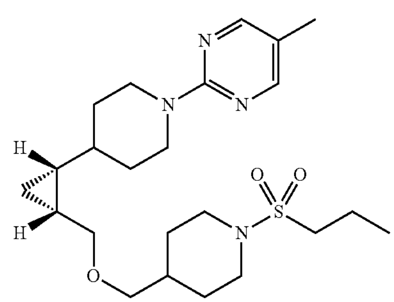 [SMILES: CCCS(=O)(=O)N1CCC(COC[C@@H]2C[C@@H]2C2CCN(c3ncc(C)cn3)CC2)CC1] |
| 3.5 | n-PRSO₂Cl | Et₃Al | 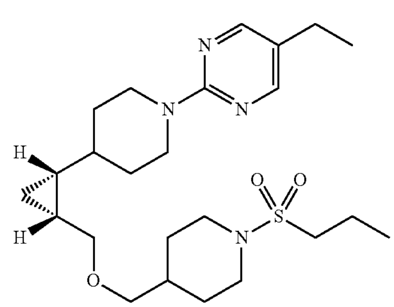 [SMILES: CCCS(=O)(=O)N1CCC(COC[C@@H]2C[C@@H]2C2CCN(c3ncc(CC)cn3)CC2)CC1] |

TABLE 3.1-continued
The following examples were prepared in a manner similar to that outlined in Scheme 3 using the appropriate reagents.
| Example | Sulfonyl Chloride | (alkyl)₃Al | Structure |
|---|---|---|---|
| 3.6 | n-PRSO₂Cl | n-PR₃Al | 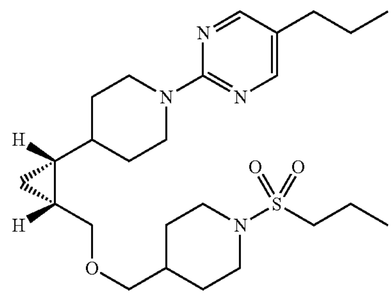 [SMILES: CCCc1cnc(N2CCC([C@H]3C[C@H]3COCC3CCN(S(=O)(=O)CCC)CC3)CC2)nc1] |
| 3.7 | n-PRSO₂Cl | i-Bu₃Al | 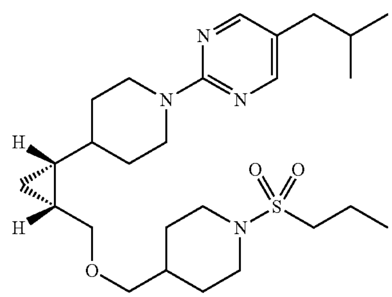 [SMILES: CCCS(=O)(=O)N1CCC(COC[C@@H]2C[C@@H]2C2CCN(c3ncc(CC(C)C)cn3)CC2)CC1] |
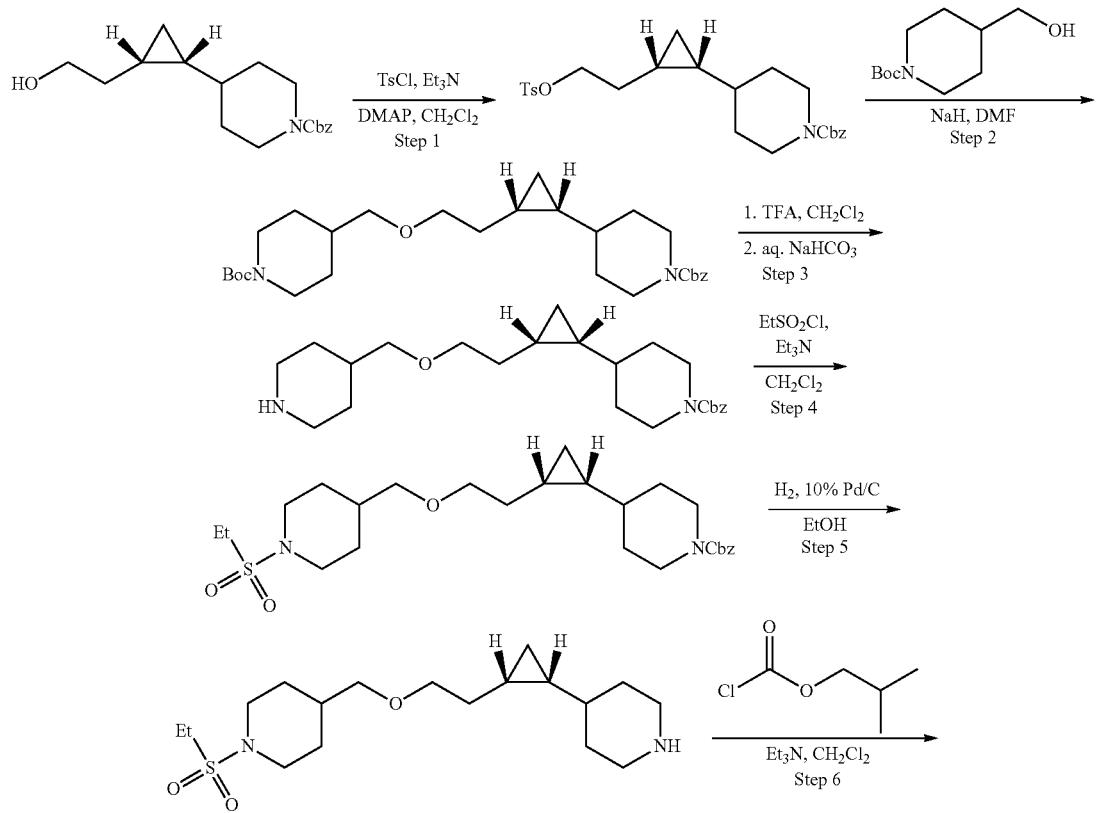
Scheme 4

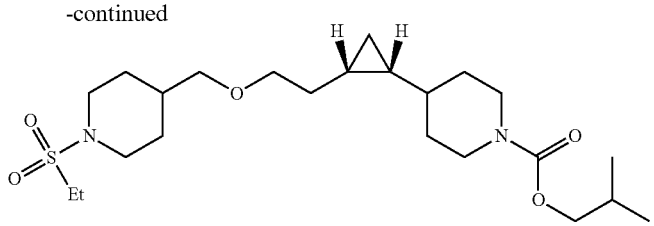

Example 4.1

Step 1

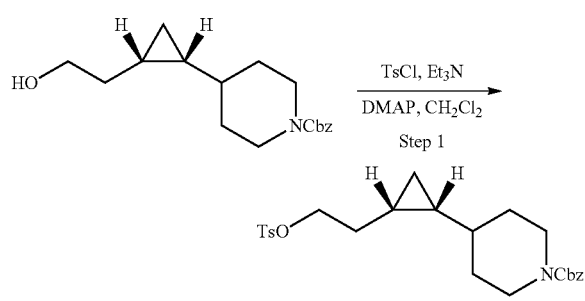

To a cooled solution of the alcohol (1.62 g, 5.34 mmol) in dichloromethane (30 mL) at 0° C. were added triethylamine (2.2 mL, 16.0 mmol), 4-dimethylaminopyridine (0.130 g, 1.07 mmol), and p-toluenesulfonyl chloride (1.53 g, 8.01 mmol). The reaction mixture was stirred at room temperature overnight. The reaction was quenched with saturated aqueous sodium hydrogen carbonate (100 mL) and extracted with dichloromethane (3×50 mL). The combined organics were washed with brine, dried over anhydrous sodium sulfate, filtered, concentrated under reduced pressure, and the resulting residue purified by silica gel column chromatography, (gradient elution, 5 to 50% ethyl acetate in heptane) to provide the tosylate as a clear oil.

Step 2

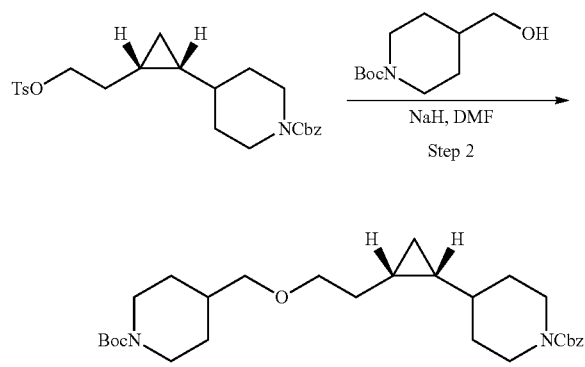

To a stirred solution tert-butyl-4-(hydroxymethyl) piperidine-1-carboxylate (3.59 g, 16.7 mmol) in DMF (60 mL) under a nitrogen atmosphere was added sodium hydride (60% dispersion in oil, 1.67 g, 41.7 mmol) and the resulting solution was stirred for 20 min. To the stirring solution was added the tosylate from Step 1 (6.37 g, 13.9 mmol) and the resulting solution was stirred under a nitrogen atmosphere for 18 h. The solution was quenched with $H_2O$ (150 mL) and partitioned with EtOAc (150 mL). The resulting layers were separated and the aqueous phase extracted with EtOAc (2×100 mL) and the combined organic extracts were washed with brine (4×50 mL), dried over anhydrous $Na_2SO_4$, filtered and concentrated under reduced pressure. Purification of the residue by column chromatography (silica gel, 0 to 40% EtOAc in hexanes) afforded the desired product as a clear oil.

Step 3

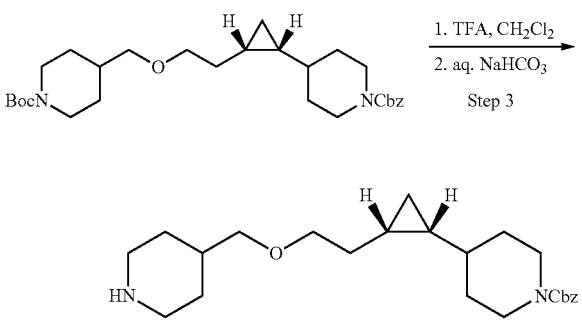

To a stirred solution of the product from Step 2 (3.0 g, 6.0 mmol) in dichloromethane (24 mL) under nitrogen atmosphere at 0° C. was added trifluoroacetic acid (8.0 mL) and the resulting solution was stirred for 20 min. The resulting solution was allowed to warm to ambient temperature and stirred at this temperature for 1.5 h. The reaction mixture was carefully quenched with saturated $NaHCO_3$ (aq.) (200 mL) and the resulting layers were separated and the aqueous phase was extracted with dichloromethane (3×100 mL). The combined organic extracts were washed with brine (3×100 mL), dried over anhydrous $Na_2SO_4$, filtered and concentrated to dryness under reduced pressure to provide the crude intermediate as a light orange oil which was used in the next step without further purification.

Step 4

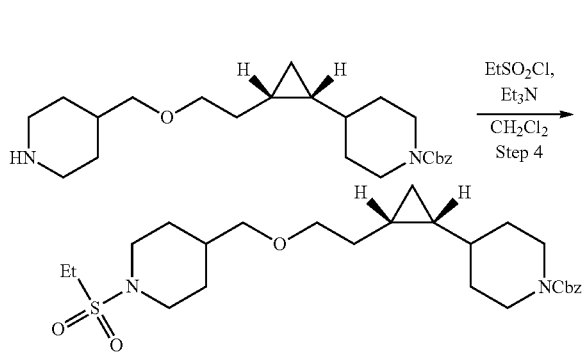

To a stirred solution of the material from Step 3 (2.4 g, 6.0 mmol) in dichloromethane (34 mL) under nitrogen atmosphere was added triethylamine (2.5 mL, 18 mmol), N,N-dimethylaminopyridine (0.15 g, 1.2 mmol), and ethyl sulfonylchloride (0.68 mL, 7.2 mmol). The resulting solution was stirred for 18 h at ambient temperature and was then diluted with saturated $NH_4Cl_{(aq.)}$ (50 mL). The resulting layers were separated and the aqueous phase extracted with dichloromethane (3×75 mL) and the combined organic extracts were concentrated under reduced pressure. Purification of the residue by CombiFlash chromatography (silica gel, 0 to 50% EtOAc in hexanes) followed by CombiFlash chromatography (silica gel, 0 to 5% methanol in dichloromethane) provided the desired product as a clear oil.

Step 5

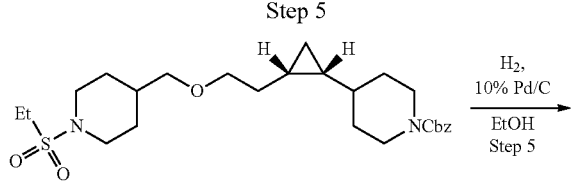

The product from Step 4 (1.6 g, 3.3 mmol) was dissolved in 200 proof EtOH (12 mL) under a nitrogen atmosphere. Nitrogen was bubbled through the solution for 20 min before Palladium (10 wt % on carbon, 0.350 g) was added. Hydrogen gas was bubbled through the resulting solution for 20 min. The mixture was stirred at ambient temperature under a hydrogen balloon atmosphere for 72 h. The resulting suspension was filtered through Celite® and rinsed with EtOH (1.2 L). The filtrate was concentrated to dryness under reduced pressure to provide the crude intermediate as a light orange film.

Step 6

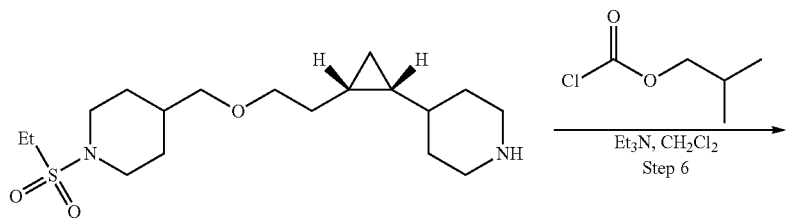

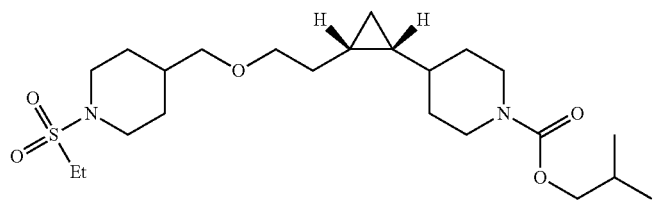

Example 4.1

To a stirred solution of the material prepared in the previous step (0.20 g, 0.55 mmol) in dichloromethane (12 mL) under nitrogen atmosphere was added triethylamine (0.23 mL, 1.6 mmol) and isobutyl chloroformate (0.11 mL, 0.82 mmol). The resulting solution was stirred for 18 h at ambient temperature and was then diluted with saturated $NH_4Cl_{(aq)}$ (30 mL). The resulting layers were separated and the aqueous phase extracted with dichloromethane (3×30 mL). The combined organic extracts were washed with brine (1×20 mL) and concentrated under reduced pressure. Purification of the obtained residue by silica gel chromatography (gradient elution, 0 to 30% EtOAc in hexanes) afforded Example 4.1 (0.17 g) as a light yellow viscous oil.

TABLE 4.1
Using the method outlined in Scheme 4 and the requisite acylating agent, the following examples were prepared:
| Acylating Agent | Example Number | Structure |
|---|---|---|
| | 4.2 | |
| | 4.3 | |
| | 4.4 | |
| | 4.5 | |
| | 4.6 | |
Scheme 5
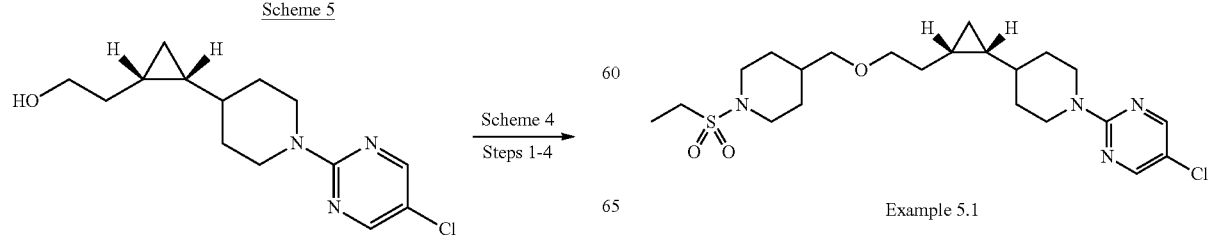
Example 5.1

Example 5.1 was prepared from the requisite alcohol via Steps 1-4 in Scheme 4.

TABLE 5.1

Using the method outlined in Steps 1 through 4 of Scheme 4 and the appropriate starting materials, the following examples were prepared:

| Alcohol | Sulfonyl Chloride | Example Number | Structure |
|---|---|---|---|
| BocN-piperidine-CH2OH | methanesulfonyl chloride | 5.2 | (structure) |
| BocN-piperidine-CH2OH | isopropylsulfonyl chloride | 5.3 | (structure) |
| BocN-piperidine-CH2OH | 3,3,3-trifluoropropylsulfonyl chloride | 5.4 | (structure) |
| BocN-piperidine-CH2OH | propylsulfonyl chloride | 5.5 | (structure) |
| BocN-piperidine-OH | propylsulfonyl chloride | 5.6 | (structure) |
| BocN-piperidine-OH | 3,3,3-trifluoropropylsulfonyl chloride | 5.7 | (structure) |

TABLE 5.1-continued

Using the method outlined in Steps 1 through 4 of Scheme 4 and the appropriate starting materials, the following examples were prepared:

| Alcohol | Sulfonyl Chloride | Example Number | Structure |
|---|---|---|---|
| BocN-piperidine-4-OH | ethanesulfonyl chloride | 5.8 | [ethylsulfonyl-piperidinyl-O-CH2CH2-cyclopropyl-piperidinyl-(5-chloropyrimidin-2-yl)] |
| BocN-piperidine-4-OH | isopropylsulfonyl chloride | 5.9 | [isopropylsulfonyl-piperidinyl-O-CH2CH2-cyclopropyl-piperidinyl-(5-chloropyrimidin-2-yl)] |
| BocN-piperidine-4-OH | methanesulfonyl chloride | 5.10 | [methylsulfonyl-piperidinyl-O-CH2CH2-cyclopropyl-piperidinyl-(5-chloropyrimidin-2-yl)] |
| BocN-azetidine-3-OH | methanesulfonyl chloride | 5.11 | [methylsulfonyl-azetidinyl-O-CH2CH2-cyclopropyl-piperidinyl-(5-chloropyrimidin-2-yl)] |

TABLE 5.1-continued

Using the method outlined in Steps 1 through 4 of Scheme 4 and the appropriate starting materials, the following examples were prepared:

| Alcohol | Sulfonyl Chloride | Example Number | Structure |
|---|---|---|---|
| BocN-azetidine-OH | isopropylsulfonyl chloride | 5.12 | isopropylsulfonyl-azetidine-O-ethyl-cyclopropyl-piperidine-pyrimidine-Cl |
| BocN-azetidine-OH | ethanesulfonyl chloride | 5.13 | ethylsulfonyl-azetidine-O-ethyl-cyclopropyl-piperidine-pyrimidine-Cl |
| BocN-azetidine-OH | 3,3,3-trifluoropropane-1-sulfonyl chloride | 5.14 | 3,3,3-trifluoropropylsulfonyl-azetidine-O-ethyl-cyclopropyl-piperidine-pyrimidine-Cl |
| Boc-(3S)-pyrrolidine-OH | 3,3,3-trifluoropropane-1-sulfonyl chloride | 5.15 | 3,3,3-trifluoropropylsulfonyl-pyrrolidine-O-ethyl-cyclopropyl-piperidine-pyrimidine-Cl |
| Boc-(3S)-pyrrolidine-OH | methanesulfonyl chloride | 5.16 | methylsulfonyl-pyrrolidine-O-ethyl-cyclopropyl-piperidine-pyrimidine-Cl |

TABLE 5.1-continued

Using the method outlined in Steps 1 through 4 of Scheme 4 and the appropriate starting materials, the following examples were prepared:

| Alcohol | Sulfonyl Chloride | Example Number | Structure |
|---|---|---|---|
| (Boc-pyrrolidin-3-ol, 3R) | ethanesulfonyl chloride | 5.17 | ethylsulfonyl-pyrrolidinyloxy-ethyl-cyclopropyl-piperidinyl-(5-chloropyrimidin-2-yl) |
| (Boc-pyrrolidin-3-ol, 3S) | ethanesulfonyl chloride | 5.18 | ethylsulfonyl-pyrrolidinyloxy-ethyl-cyclopropyl-piperidinyl-(5-chloropyrimidin-2-yl) |
| (Boc-pyrrolidin-3-ol, 3S) | methanesulfonyl chloride | 5.19 | methylsulfonyl-pyrrolidinyloxy-ethyl-cyclopropyl-piperidinyl-(5-chloropyrimidin-2-yl) |
| (Boc-pyrrolidin-3-ol, 3S) | 3,3,3-trifluoropropane-1-sulfonyl chloride | 5.20 | (3,3,3-trifluoropropyl)sulfonyl-pyrrolidinyloxy-ethyl-cyclopropyl-piperidinyl-(5-chloropyrimidin-2-yl) |
| (Boc-pyrrolidin-3-ol, 3R) | propane-2-sulfonyl chloride | 5.21 | isopropylsulfonyl-pyrrolidinyloxy-ethyl-cyclopropyl-piperidinyl-(5-chloropyrimidin-2-yl) |

TABLE 5.1-continued

Using the method outlined in Steps 1 through 4 of Scheme 4 and the appropriate starting materials, the following examples were prepared:

| Alcohol | Sulfonyl Chloride | Example Number | Structure |
|---|---|---|---|
|  |  | 5.22 | 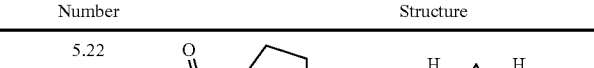 |

Scheme 6

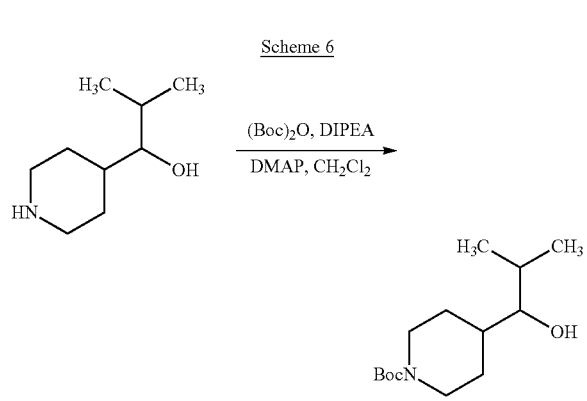

To a solution of racemic 2-methyl-1-(piperidin-4-yl)propan-1-ol (1.00 g, 6.36 mmol) in THF (65 mL) at room temperature was added N,N-diisopropylethylamine (1.6 mL, 9.54 mmol) and 4-dimethylaminopyridine (0.07 g, 0.63 mmol), followed by di-tert-butyl dicarbonate (1.53 g, 6.99 mmol). The reaction mixture was stirred at room temperature overnight. The reaction mixture was quenched with water (100 mL) and extracted with methylene chloride (3×100 mL). The combined organic layers were washed with brine, dried over anhydrous sodium sulfate and concentrated under reduced pressure. The residue was purified by column chromatography (SiO$_2$, gradient elution, 0-10% methanol in methylene chloride) to provide the desired product as a white solid.

Scheme 7

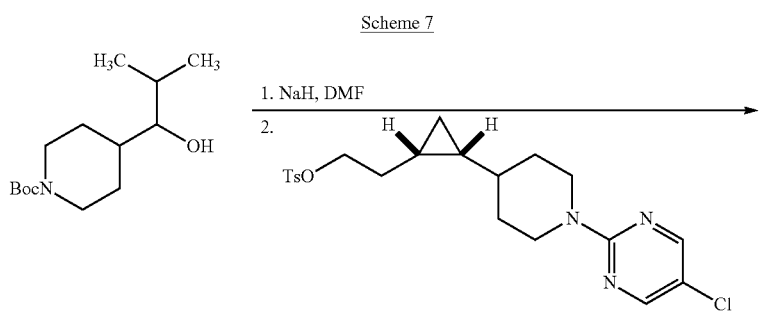

Step 1

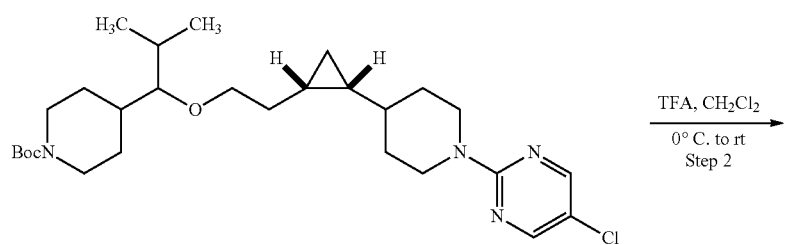

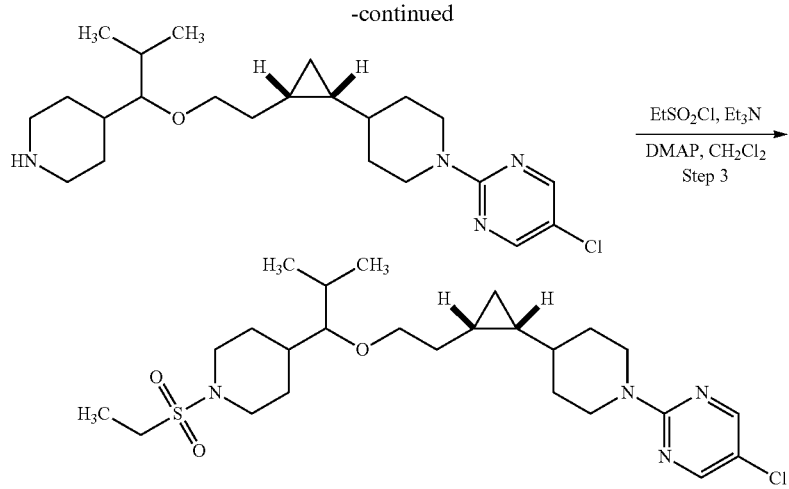

Example 7.1

Step 1

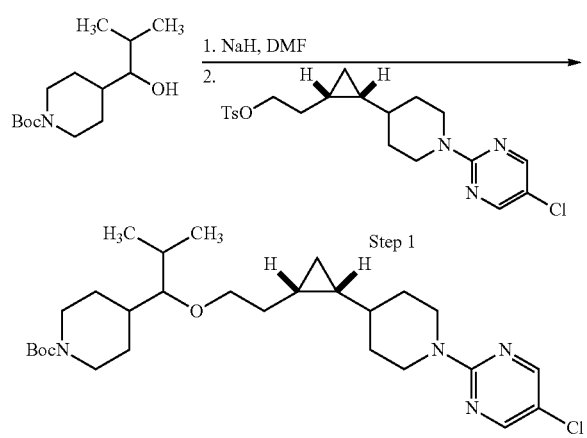

To a solution of tert-butyl 4-(1-hydroxy-2-methylpropyl) piperidine-1-carboxylate (177 mg, 0.688 mmol) in DMF (6 mL) at room temperature was added sodium hydride (60% dispersion in mineral oil, 69 mg, 1.72 mmol) and the mixture was stirred at room temperature for 1 h. After this time, the tosylate prepared in Scheme 5 (250 mg, 0.573) was added, was stirred for 4 h, then was heated at 50° C. overnight. The reaction was cooled to room temperature, quenched with water (50 mL), extracted with ethyl acetate (3×50 mL), and the combined organics were washed with 5% lithium chloride solution (25 mL), brine, dried over anhydrous sodium sulfate and concentrated under vacuum. The residue was purified by silica gel column chromatography, (0-15% ethyl acetate in heptane) to provide the desired product (35 mg, 17%) as a clear oil.

Step 2

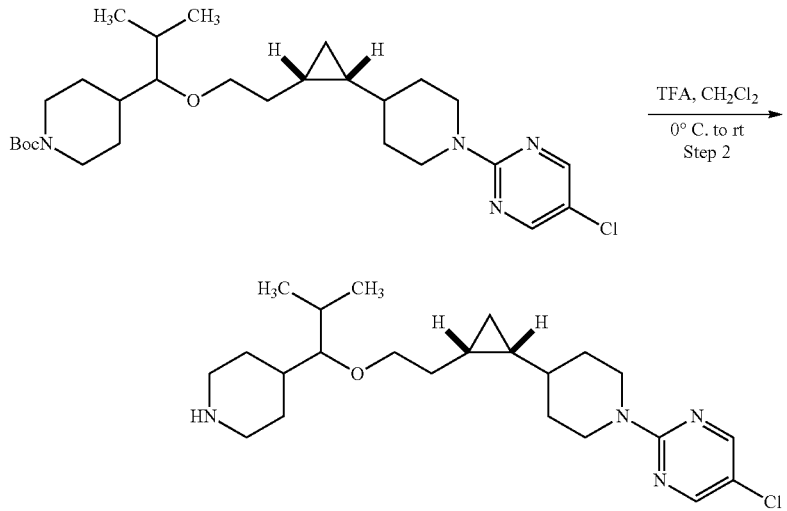

To a cooled solution of the product from Step 1 (35 mg, 0.067 mmol) in methylene chloride (4 mL) at 0° C., was added TFA (0.08 mL, 1.01 mmol) dropwise and the resulting reaction was warmed to room temperature and stirred for 16 h. After this time, the reaction was basified with sodium hydrogen carbonate (100 mL) to pH 8, extracted with methylene chloride (3×25 mL), and the combined organics were washed with brine, dried over anhydrous sodium sulfate, filtered and concentrated under reduced pressure to provide the desired amine as a clear oil.

Step 3

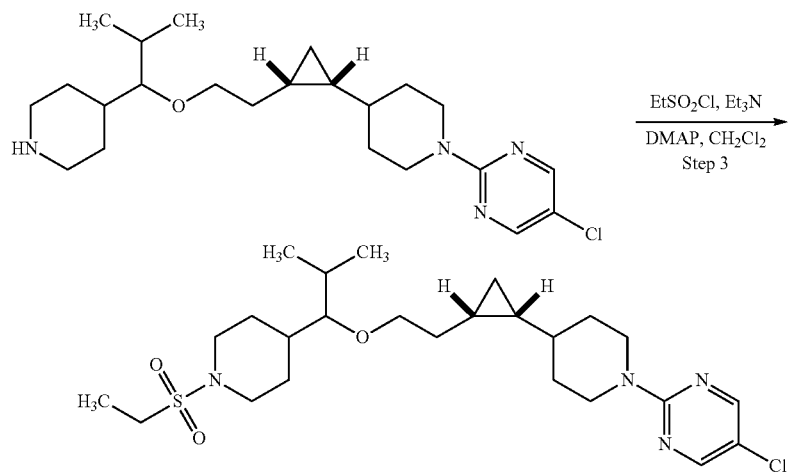

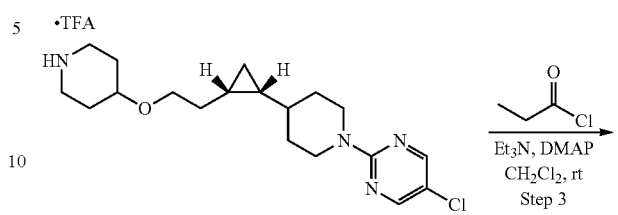

Example 7.1

To a solution of the amine from Step 2 (23 mg, 0.055 mmol) in methylene chloride (4 mL) at room temperature were added triethylamine (0.02 mL, 0.164 mmol), 4-dimethylaminopyridine (1 mg, 0.011 mmol), and ethanesulfonyl chloride (0.01 mL, 0.109 mmol). The reaction was stirred at room temperature overnight. The reaction mixture was concentrated and the residue purified by silica gel chromatography (gradient elution, 0-25% ethyl acetate in heptane) to afford a brown oil which was dried in a vacuum oven overnight at 70° C. to provide Example 7.1 as a brown oil.

Example 8

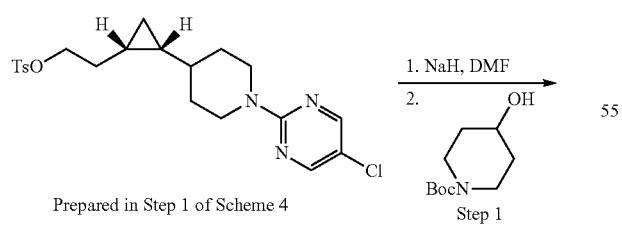

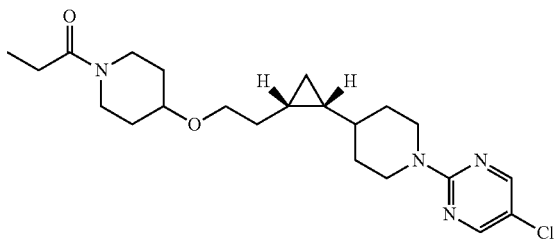

Example 8.1

Step 1

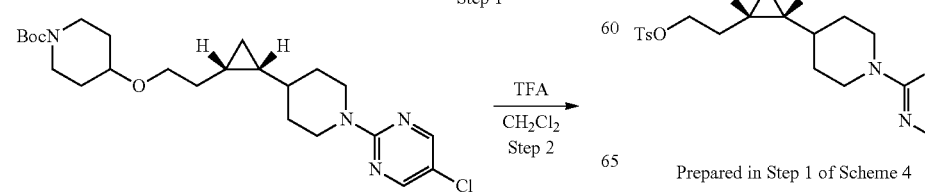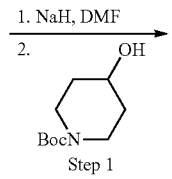

-continued

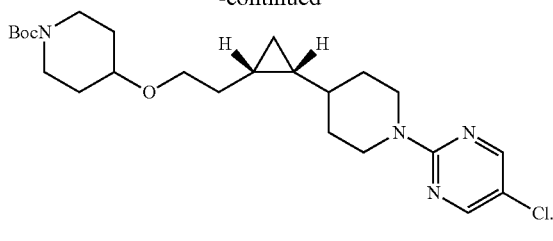

A solution of tert-butyl 4-hydroxypiperidine-1-carboxylate (1.38 g, 6.9 mmol) in DMF (10 mL) was added dropwise to a stirred suspension of sodium hydride (60% dispersion in mineral oil, 0.55 g, 13.7 mmol) in DMF (5 mL) at 0° C. The reaction was stirred for 1 h then the tosylate prepared in Step 1 of Scheme 4 (1.5 g, 3.4 mmol) was added and the reaction was stirred overnight at room temperature. The reaction was quenched with water (10 mL) and diluted with ethyl acetate (100 mL). The resulting layers were separated and the aqueous phase was extracted with ethyl acetate (2×100 mL). The combined organic extracts were dried over anhydrous sodium sulfate, filtered and concentrated under reduced pressure. Purification of the obtained residue by silica gel chromatography (gradient elution, 0 to 15% EtOAc in heptane) provided the desired product as a light yellow oil.

Step 2

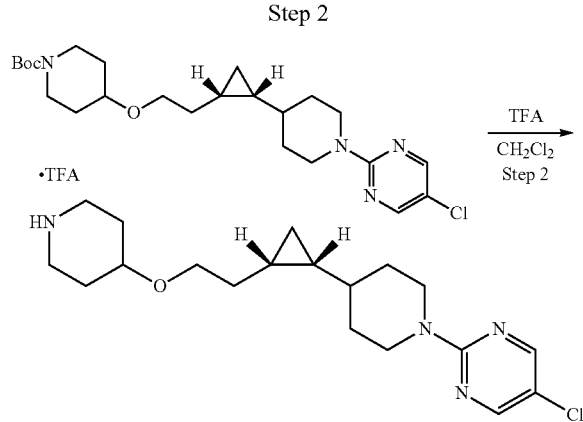

A solution of the product from the previous step (1.4 g, 3.0 mmol) in dichloromethane (9.6 mL) was treated with trifluoroacetic acid (2.4 mL, 31 mmol). The reaction was stirred for 3 h and then concentrated under reduced pressure to provide the desired product as a yellow semi-solid.

Step 3

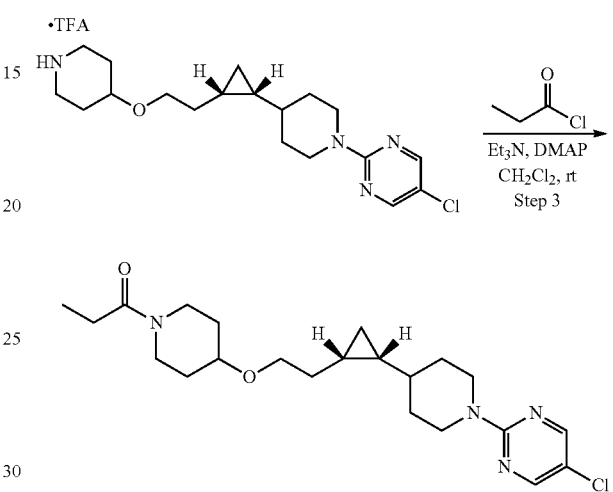

Example 8.1

To a stirred solution of the amine salt prepared in the previous step (0.15 g, 0.32 mmol) in dichloromethane (2 mL) under a nitrogen atmosphere was added triethylamine (0.13 mL, 0.97 mmol), N,N-dimethylpyridin-4-amine (0.008 g, 0.06 mmol) and propionyl chloride (0.07 mL, 0.81 mmol). The resulting solution was stirred overnight at ambient temperature and then concentrated under reduced pressure. Purification of the obtained residue by silica gel chromatography (gradient elution, 0 to 3% methanol in dichloromethane) provided Example 8.1 as a clear oil.

TABLE 8.1

Using a method similar to that outlined in Scheme 8 and the requisite acid chloride, the following examples were prepared:

| Acid Chloride | Example Number | Structure |
| --- | --- | --- |
|  | 8.2 |  |

Scheme 9

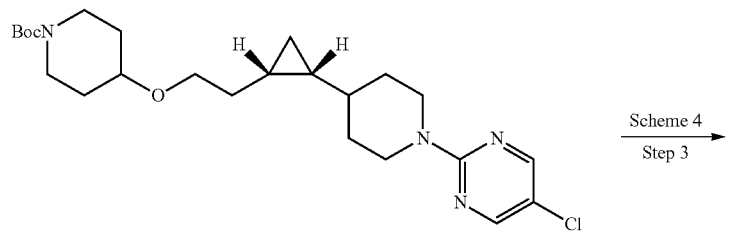

Prepared in Step 1 of Scheme 8

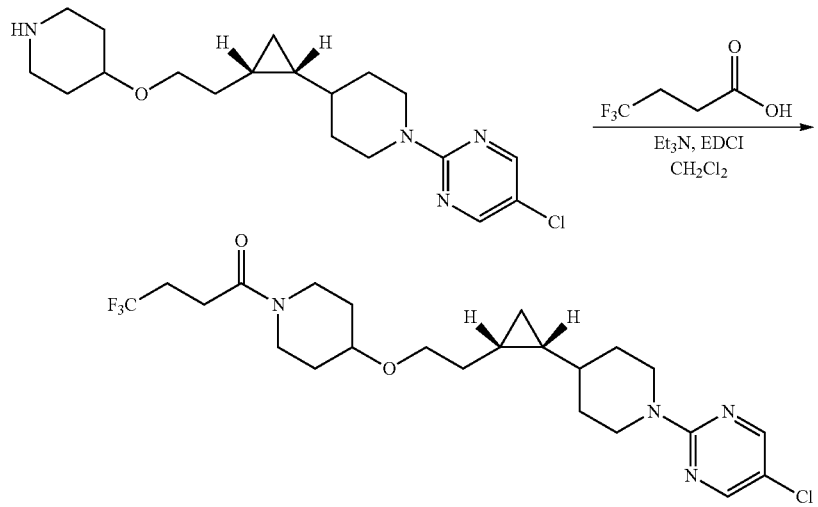

Example 9.1

The material prepared in Step 1 of Scheme 8 was subjected to conditions similar to those described in Step 3 of Scheme 4 to provide the desired amine.

Step 1

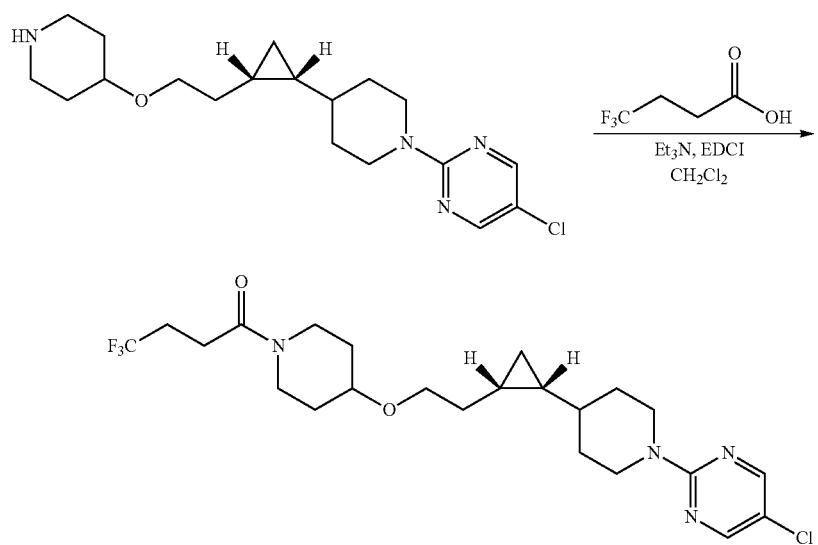

Example 9.1

To a stirred solution of 4,4,4-trifluorobutanoic acid (0.05 g, 0.39 mmol) in dichloromethane (1 mL) was added EDC (0.09 g, 0.49 mmol) and triethylamine (0.22 mL, 1.6 mmol). After stirring for 5 min, 5-chloro-2-(4-((1R,2S)-2-(2-(piperidin-4-yloxy)ethyl)cyclopropyl)piperidin-1-yl)pyrimidine (0.15 g, 0.32 mmol) was added and the mixture was stirred overnight at room temperature. The solution was concentrated under reduced pressure and purification of the obtained residue by silica gel chromatography (gradient elution, 0 to 20% ethyl acetate in heptane) provided Example 9.1 as a light yellow oil.

TABLE A

The compounds below were prepared according to the detailed procedures provided above. The mass spectral data are included in the table and represent [M + H]+ unless otherwise noted.

| Structure | Example Number | M.S. Data [M + H]+ |
|---|---|---|
| 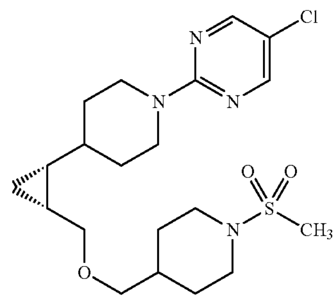 [SMILES: CS(=O)(=O)N1CCC(COC[C@@H]2C[C@@H]2C2CCN(c3ncc(Cl)cn3)CC2)CC1] | 1.1 | 443.2 |
| 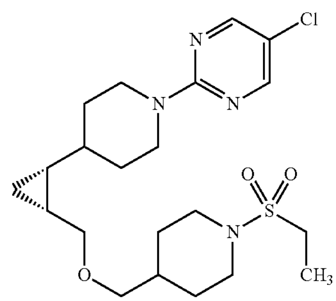 [SMILES: CCS(=O)(=O)N1CCC(COC[C@@H]2C[C@@H]2C2CCN(c3ncc(Cl)cn3)CC2)CC1] | 1.2 | 457.3 |
| 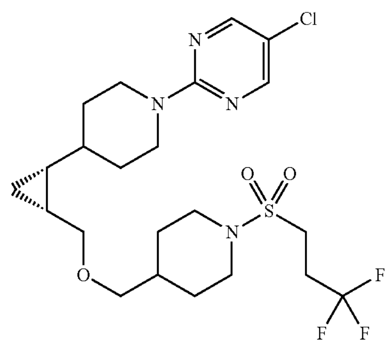 [SMILES: O=S(=O)(CCC(F)(F)F)N1CCC(COC[C@@H]2C[C@@H]2C2CCN(c3ncc(Cl)cn3)CC2)CC1] | 1.3 | 525.3 |
| 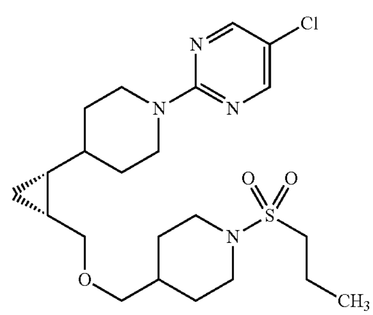 [SMILES: CCCS(=O)(=O)N1CCC(COC[C@@H]2C[C@@H]2C2CCN(c3ncc(Cl)cn3)CC2)CC1] | 1.4 | 471.3 |

TABLE A-continued
The compounds below were prepared according to the detailed procedures provided above. The mass spectral data are included in the table and represent [M + H]⁺ unless otherwise noted.
| Structure | Example Number | M.S. Data [M + H]⁺ |
|---|---|---|
| 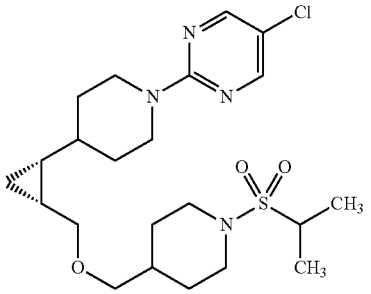 [SMILES: CC(C)S(=O)(=O)N1CCC(COC[C@@H]2C[C@@H]2C2CCN(c3ncc(Cl)cn3)CC2)CC1] | 1.5 | 471.3 |
| 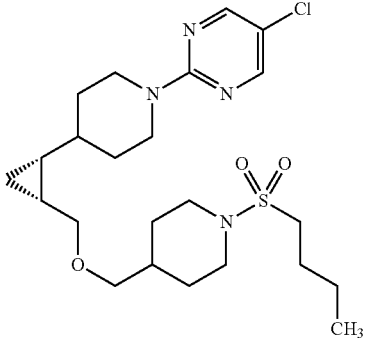 [SMILES: CCCCS(=O)(=O)N1CCC(COC[C@@H]2C[C@@H]2C2CCN(c3ncc(Cl)cn3)CC2)CC1] | 1.6 | 485.3 |
| 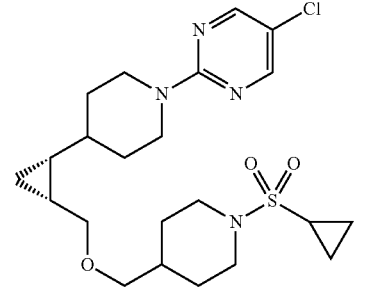 [SMILES: O=S(=O)(C1CC1)N1CCC(COC[C@@H]2C[C@@H]2C2CCN(c3ncc(Cl)cn3)CC2)CC1] | 1.7 | 469.3 |
| 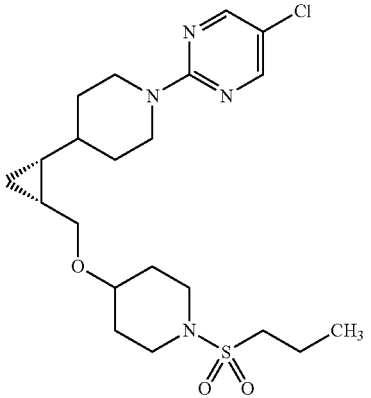 [SMILES: CCCS(=O)(=O)N1CCC(OC[C@@H]2C[C@@H]2C2CCN(c3ncc(Cl)cn3)CC2)CC1] | 2.2 | 457.3 |

TABLE A-continued

The compounds below were prepared according to the detailed procedures provided above. The mass spectral data are included in the table and represent [M + H]+ unless otherwise noted.

| Structure | Example Number | M.S. Data [M + H]+ |
|---|---|---|
| (structure) | 2.1 | 471.3 |
| (structure) | 3.5 | 465.3 |
| (structure) | 3.6 | 479.3 |
| (structure) | 3.7 | 493.3 |

TABLE A-continued

The compounds below were prepared according to the detailed procedures provided above. The mass spectral data are included in the table and represent [M + H]+ unless otherwise noted.

| Structure | Example Number | M.S. Data [M + H]+ |
|---|---|---|
| 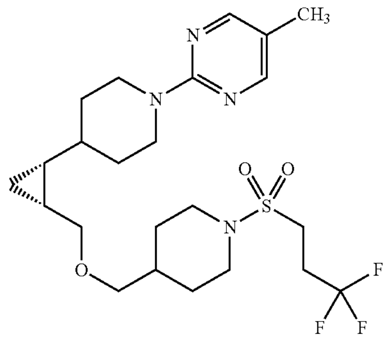 [SMILES: Cc1cnc(N2CCC([C@H]3C[C@H]3COCC3CCN(S(=O)(=O)CCC(F)(F)F)CC3)CC2)nc1] | 3.1 | 505.3 |
| 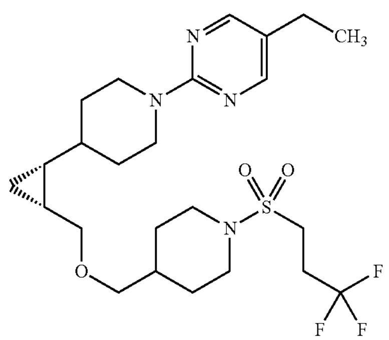 [SMILES: CCc1cnc(N2CCC([C@H]3C[C@H]3COCC3CCN(S(=O)(=O)CCC(F)(F)F)CC3)CC2)nc1] | 3.2 | 519.3 |
| 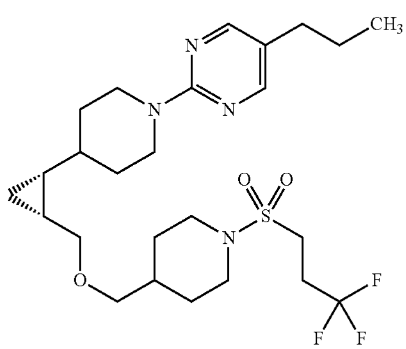 [SMILES: CCCc1cnc(N2CCC([C@H]3C[C@H]3COCC3CCN(S(=O)(=O)CCC(F)(F)F)CC3)CC2)nc1] | 3.3 | 533.3 |
| 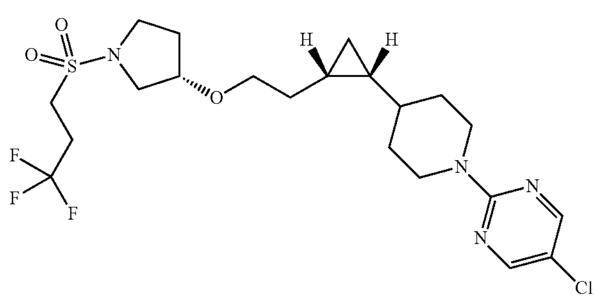 [SMILES: O=S(=O)(CCC(F)(F)F)N1CC[C@H](OCC[C@@H]2C[C@@H]2C2CCN(c3ncc(Cl)cn3)CC2)C1] | 5.15 | 511 |

TABLE A-continued

The compounds below were prepared according to the detailed procedures provided above. The mass spectral data are included in the table and represent [M + H]+ unless otherwise noted.

| Structure | Example Number | M.S. Data [M + H]+ |
|---|---|---|
| 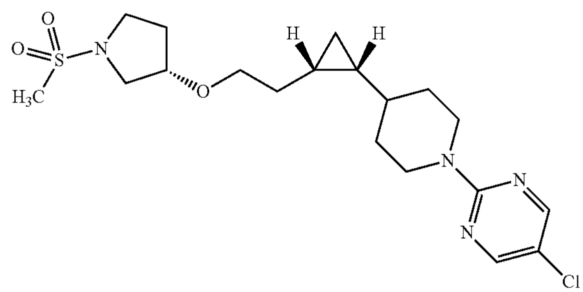 [SMILES: CS(=O)(=O)N1CC[C@H](OCC[C@@H]2C[C@@H]2C2CCN(c3ncc(Cl)cn3)CC2)C1] | 5.16 | 429 |
| 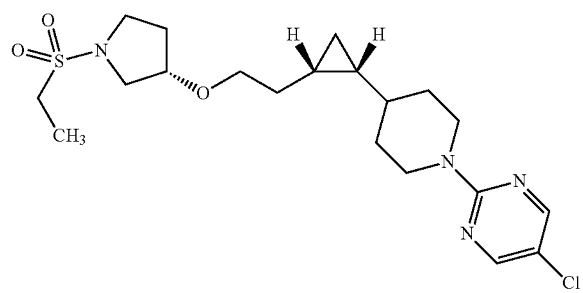 [SMILES: CCS(=O)(=O)N1CC[C@H](OCC[C@@H]2C[C@@H]2C2CCN(c3ncc(Cl)cn3)CC2)C1] | 5.17 | 443 |
| 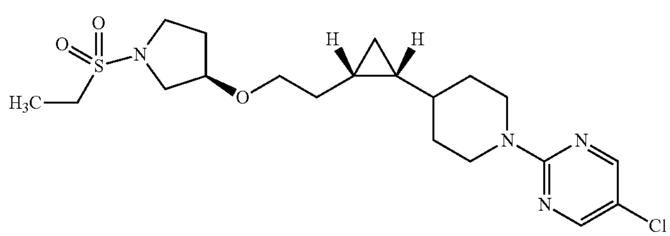 [SMILES: CCS(=O)(=O)N1CC[C@@H](OCC[C@@H]2C[C@@H]2C2CCN(c3ncc(Cl)cn3)CC2)C1] | 5.18 | 443 |
| 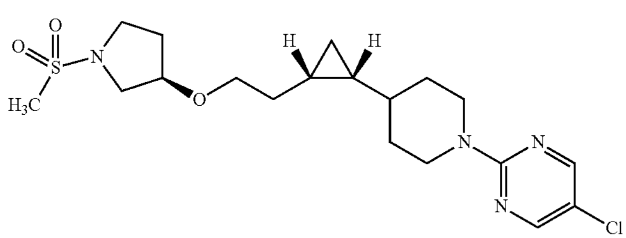 [SMILES: CS(=O)(=O)N1CC[C@@H](OCC[C@@H]2C[C@@H]2C2CCN(c3ncc(Cl)cn3)CC2)C1] | 5.19 | 429 |
| 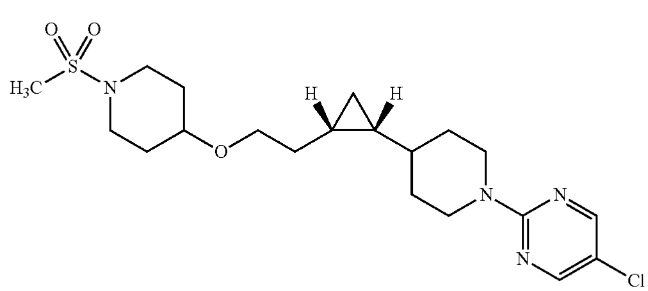 [SMILES: CS(=O)(=O)N1CCC(OCC[C@@H]2C[C@@H]2C2CCN(c3ncc(Cl)cn3)CC2)CC1] | 5.1 | 443 |

TABLE A-continued

The compounds below were prepared according to the detailed procedures provided above. The mass spectral data are included in the table and represent [M + H]⁺ unless otherwise noted.

| Structure | Example Number | M.S. Data [M + H]⁺ |
|---|---|---|
| 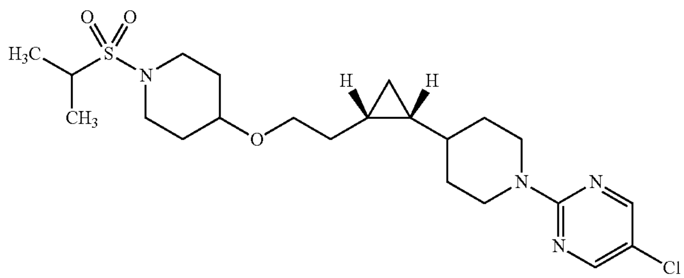 [SMILES: CC(C)S(=O)(=O)N1CCC(OCC[C@@H]2C[C@@H]2C2CCN(c3ncc(Cl)cn3)CC2)CC1] | 5.9 | 471 |
| 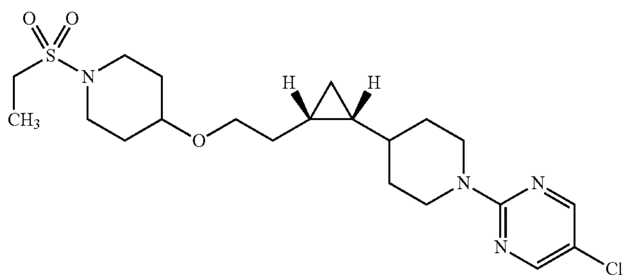 [SMILES: CCS(=O)(=O)N1CCC(OCC[C@@H]2C[C@@H]2C2CCN(c3ncc(Cl)cn3)CC2)CC1] | 5.8 | 457 |
| 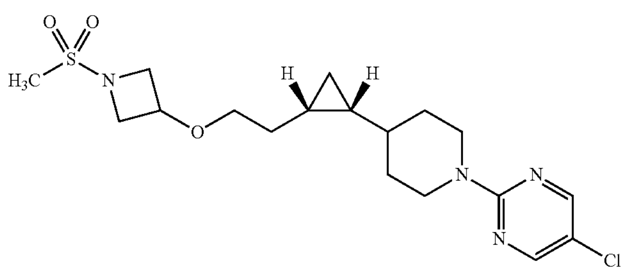 [SMILES: CS(=O)(=O)N1CC(OCC[C@@H]2C[C@@H]2C2CCN(c3ncc(Cl)cn3)CC2)C1] | 5.11 | 415 |
| 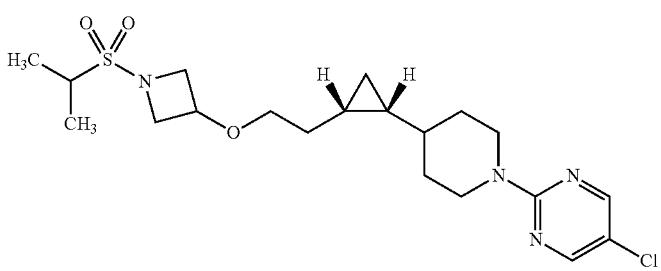 [SMILES: CC(C)S(=O)(=O)N1CC(OCC[C@@H]2C[C@@H]2C2CCN(c3ncc(Cl)cn3)CC2)C1] | 5.12 | 443 |
| 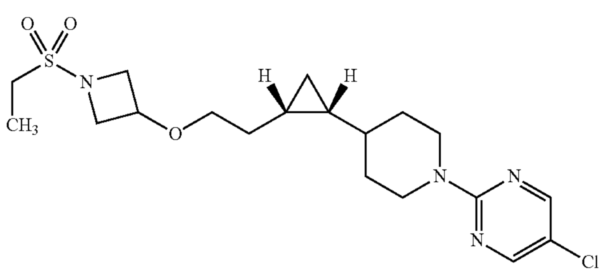 [SMILES: CCS(=O)(=O)N1CC(OCC[C@@H]2C[C@@H]2C2CCN(c3ncc(Cl)cn3)CC2)C1] | 5.13 | 429 |

TABLE A-continued

The compounds below were prepared according to the detailed procedures provided above. The mass spectral data are included in the table and represent [M + H]⁺ unless otherwise noted.

| Structure | Example Number | M.S. Data [M + H]⁺ |
|---|---|---|
| | 5.2 | 511 |
| 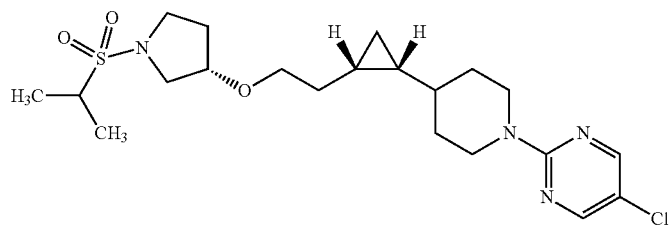 [SMILES: CC(C)S(=O)(=O)N1CC[C@H](OCC[C@@H]2C[C@@H]2C2CCN(c3ncc(Cl)cn3)CC2)C1] | 5.21 | 457 |
| | 5.2 | 457 |
| 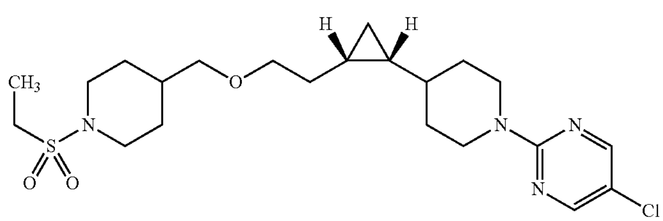 [SMILES: CCS(=O)(=O)N1CCC(COCC[C@@H]2C[C@@H]2C2CCN(c3ncc(Cl)cn3)CC2)CC1] | 5.1 | 471 |
| 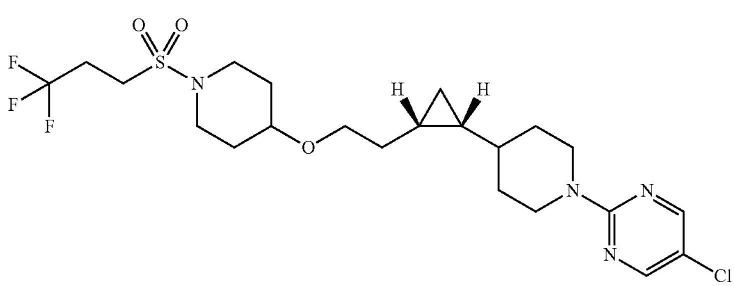 [SMILES: O=S(=O)(CCC(F)(F)F)N1CCC(OCC[C@@H]2C[C@@H]2C2CCN(c3ncc(Cl)cn3)CC2)CC1] | 5.7 | 525 |
| 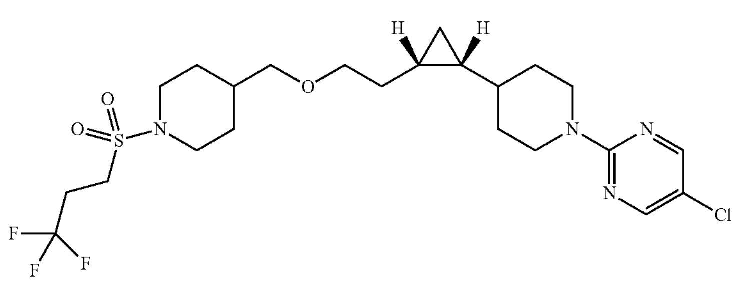 [SMILES: O=S(=O)(CCC(F)(F)F)N1CCC(COCC[C@@H]2C[C@@H]2C2CCN(c3ncc(Cl)cn3)CC2)CC1] | 5.4 | 539 |

TABLE A-continued

The compounds below were prepared according to the detailed procedures provided above. The mass spectral data are included in the table and represent [M + H]+ unless otherwise noted.

| Structure | Example Number | M.S. Data [M + H]+ |
|---|---|---|
| 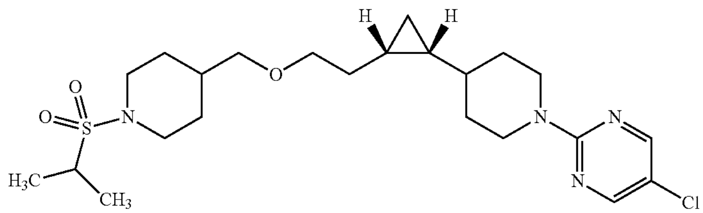 [SMILES: CC(C)S(=O)(=O)N1CCC(COCC[C@@H]2C[C@@H]2C2CCN(c3ncc(Cl)cn3)CC2)CC1] | 5.3 | 485 |
| 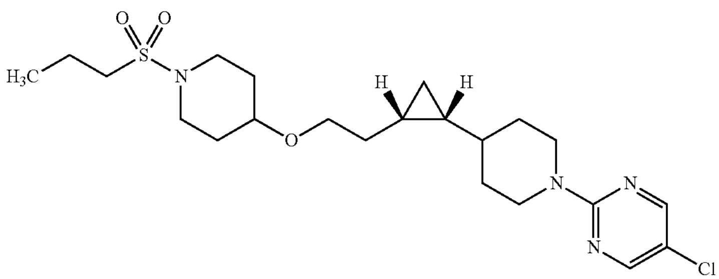 [SMILES: CCCS(=O)(=O)N1CCC(OCC[C@@H]2C[C@@H]2C2CCN(c3ncc(Cl)cn3)CC2)CC1] | 5.6 | 471 |
| 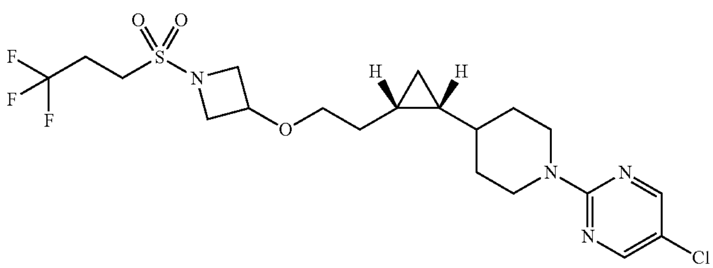 [SMILES: O=S(=O)(CCC(F)(F)F)N1CC(OCC[C@@H]2C[C@@H]2C2CCN(c3ncc(Cl)cn3)CC2)C1] | 5.14 | 497 |
| 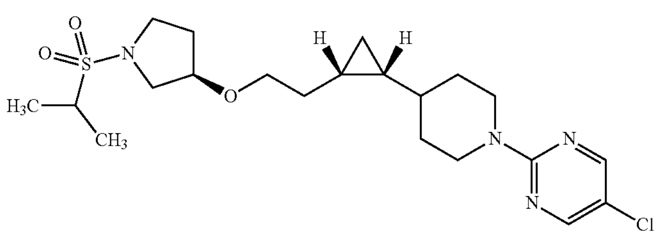 [SMILES: CC(C)S(=O)(=O)N1CC[C@@H](OCC[C@@H]2C[C@@H]2C2CCN(c3ncc(Cl)cn3)CC2)C1] | 5.22 | 457 |
| 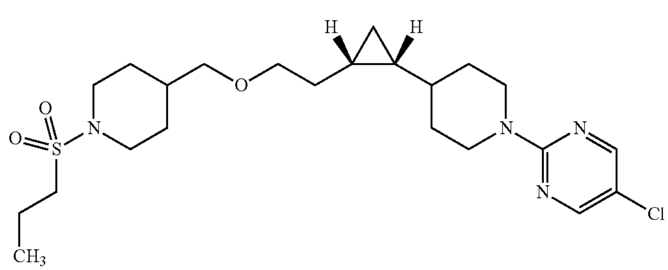 [SMILES: CCCS(=O)(=O)N1CCC(COCC[C@@H]2C[C@@H]2C2CCN(c3ncc(Cl)cn3)CC2)CC1] | 5.5 | 485 |
| 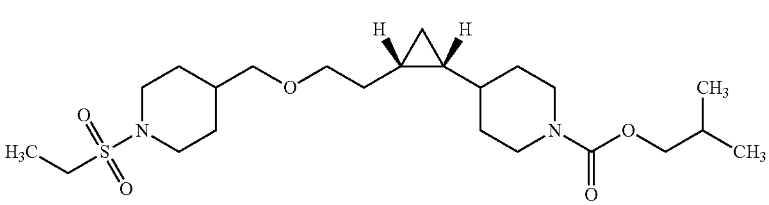 [SMILES: CCS(=O)(=O)N1CCC(COCC[C@@H]2C[C@@H]2C2CCN(C(=O)OCC(C)C)CC2)CC1] | 4.1 | 459 |

TABLE A-continued

The compounds below were prepared according to the detailed procedures provided above. The mass spectral data are included in the table and represent [M + H]⁺ unless otherwise noted.

| Structure | Example Number | M.S. Data [M + H]⁺ |
|---|---|---|
| 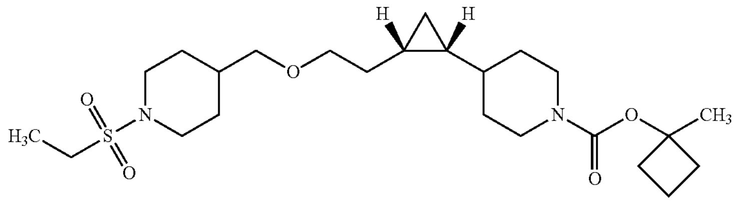 [SMILES: CCS(=O)(=O)N1CCC(COCC[C@@H]2C[C@@H]2C2CCN(C(=O)OC3(C)CCC3)CC2)CC1] | 4.2 | 471 |
| 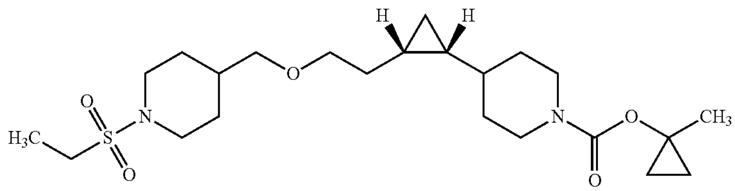 [SMILES: CCS(=O)(=O)N1CCC(COCC[C@@H]2C[C@@H]2C2CCN(C(=O)OC3(C)CC3)CC2)CC1] | 4.3 | 457 |
| 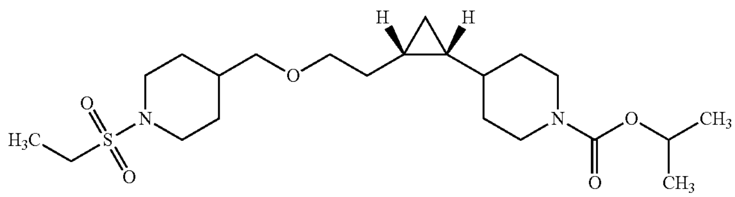 [SMILES: CCS(=O)(=O)N1CCC(COCC[C@@H]2C[C@@H]2C2CCN(C(=O)OC(C)C)CC2)CC1] | 4.4 | 445 |
| 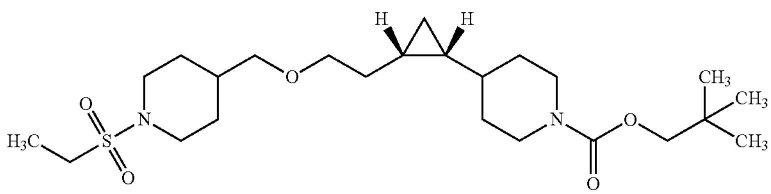 [SMILES: CCS(=O)(=O)N1CCC(COCC[C@@H]2C[C@@H]2C2CCN(C(=O)OCC(C)(C)C)CC2)CC1] | 4.6 | 473 |
| 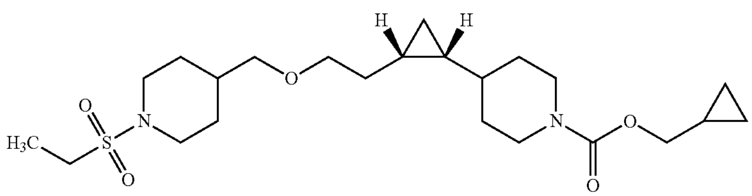 [SMILES: CCS(=O)(=O)N1CCC(COCC[C@@H]2C[C@@H]2C2CCN(C(=O)OCC3CC3)CC2)CC1] | 4.5 | 457 |
| 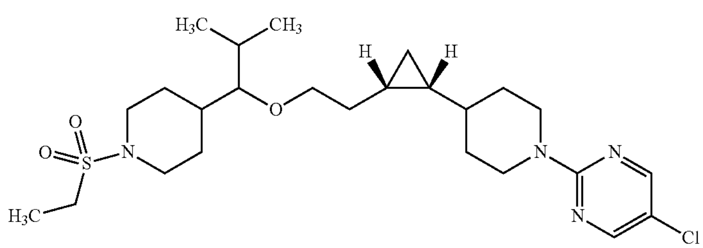 [SMILES: CCS(=O)(=O)N1CCC(C(OCC[C@@H]2C[C@@H]2C2CCN(c3ncc(Cl)cn3)CC2)C(C)C)CC1] | 7.1 | 513 |
| 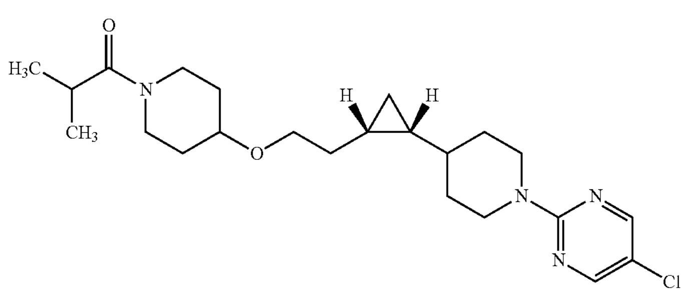 [SMILES: CC(C)C(=O)N1CCC(OCC[C@@H]2C[C@@H]2C2CCN(c3ncc(Cl)cn3)CC2)CC1] | 8.2 | 435 |

TABLE A-continued

The compounds below were prepared according to the detailed procedures provided above. The mass spectral data are included in the table and represent [M + H]+ unless otherwise noted.

| Structure | Example Number | M.S. Data [M + H]+ |
|---|---|---|
| 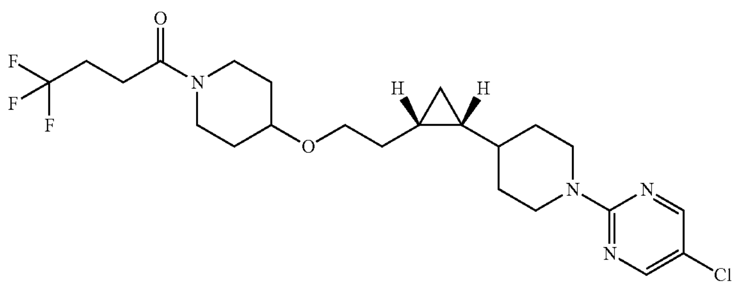 [SMILES: O=C(CCC(F)(F)F)N1CCC(OCC[C@@H]2C[C@@H]2C2CCN(c3ncc(Cl)cn3)CC2)CC1] | 9.1 | 489 |
| 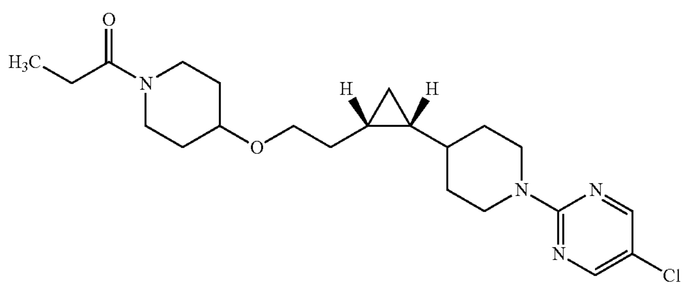 [SMILES: CCC(=O)N1CCC(OCC[C@@H]2C[C@@H]2C2CCN(c3ncc(Cl)cn3)CC2)CC1] | 8.1 | 421 |

Measurement of GPR119 Signaling Using LANCE 384-Well cAMP Kit

Human embryonic kidney (HEK) 293 cell lines stably transfected with human GPR119 were maintained in DMEM media containing FBS, penicillin-streptomycin, HEPES, and hygromycin. For the cAMP assay, the transfected cells were harvested using a non-enzymatic cell dissociation solution (GIBCO 2672), pelleted and resuspended in stimulation buffer (DMEM, 25 mM Hepes, 0.1% BSA, pH 7.4 in the presence of 1000M phosphodiesterase inhibitors). The adenylate cyclase assay was constructed following the LANCE™ cAMP Kit (Perkin Elmer, AD0264) instructions. Briefly, cells with Alexa Fluor® 647-anti cAMP antibody were incubated with 10 point series diluted test article in stimulation buffer with a final concentration of 2.5% DMSO for 45 minutes. The reaction was stopped by incubating with the supplied detection buffer containing the europium chelate of the Eu-SA/Biotin-cAMP tracer for 3 hours. The assay was performed in duplicate in a 384 well plate for duplicate plates. Fluorescence at 665 nm was measured using a PHERAstar instrument. Basal activity was determined using a DMSO control and maximum response was defined as cAMP stimulation produced by an internal agonist control. Standard cAMP concentrations were assayed concurrently for conversion of fluorescence signal to cAMP level. The data was analyzed using 4-parameter curve fit in Microsoft Excel.

The Examples of this case show inflection points, denoted as $EC_{50}$ values, less than 3000 nM when tested in the above assays, hence, compounds of the present invention are surprisingly potent as GPR119 agonists.

Example of a Pharmaceutical Formulation

As a specific embodiment of an oral composition of a compound of the present invention, 50 mg of any of the examples is formulated with sufficient finely divided lactose to provide a total amount of 580 to 590 mg to fill a size O hard gelatin capsule.

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:

1. A compound represented by the formula:

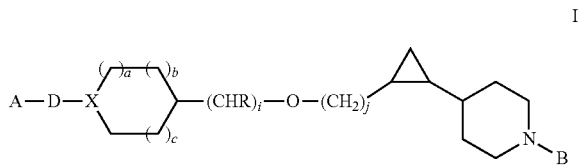

or a pharmaceutically acceptable salt thereof, wherein:
a, b and c are each 0 or 1, such that one of a, b and c is 1, and the remaining two of a, b and c are either 0 or 1, such that a 4-6 membered ring is defined;
A represents $C_{1-6}$alkyl, halo$C_{1-6}$alkyl, $C_{1-6}$alkoxy$C_{1-6}$alkyl, hydroxy$C_{1-6}$alkyl;
D represents $SO_2$ or C(O);
X represents a C or N atom;
R represents H, $C_{1-6}$alkyl or halo$C_{1-6}$alkyl;
i and j independently represent integers selected from 0, 1 and 2, such that i plus j is 1, 2 or 3;
B represents (a) a 5-6 membered heteroaryl ring 2-3 heteroatoms, 1-3 of which are nitrogen atoms and 0-1 of which is an oxygen or sulfur atom, or (b) $CO_2R^1$, said heteroaryl group (a) being optionally substituted with 1-3 groups selected from R²;
R¹ is selected from the group consisting of: $C_{1-6}$alkyl, halo$C_{1-6}$alkyl, phenyl and $C_{1-6}$alkyl-phenyl; and
each R² is independently selected from halo, $C_{1-6}$alkyl, $C_{1-4}$hydroxyalkyl and halo$C_{1-6}$alkyl.

2. A compound in accordance with claim 1, or a pharmaceutically acceptable salt thereof, wherein X represents a nitrogen atom.

3. A compound in accordance with claim 1, or a pharmaceutically acceptable salt thereof, wherein X is N and the moiety:

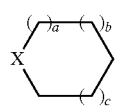

represents a member selected from the group consisting of: piperidine, pyrrolidine and azetedine.

4. A compound in accordance with claim 1, or a pharmaceutically acceptable salt thereof, wherein A represents a member selected from the group consisting of: methyl, ethyl, n-propyl, isopropyl, n-butyl, cyclopropyl and trifluoropropyl.

5. A compound in accordance with claim 1, or a pharmaceutically acceptable salt thereof, wherein R represents H; i represents 0-2 and j represents 0-2, such that the sum of i and j is 1-3.

6. A compound in accordance with claim 1, or a pharmaceutically acceptable salt thereof, wherein B represents

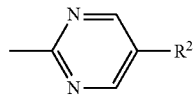

and R² is selected from the group consisting of chloro and bromo, $C_{1-4}$ alkyl, $C_{1-4}$hydroxyalkyl and $C_{1-4}$haloalkyl, in which the halo portion is selected from fluoro, chloro, bromo and iodo.

7. A compound in accordance with claim 1, or a pharmaceutically acceptable salt thereof, wherein B represents $CO_2R^1$, and R¹ is selected from the group consisting of $C_{1-6}$alkyl and $C_{1-6}$haloalkyl.

8. A compound in accordance with claim 1, or a pharmaceutically acceptable salt thereof, wherein:
A represents a member selected from the group consisting of: methyl, ethyl, n-propyl, isopropyl, n-butyl, cyclopropyl and trifluoropropyl;
X represents a nitrogen atom;
such that the moiety:

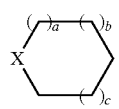

represents a member selected from the group consisting of: piperidine, pyrrolidine and azetedine;
R represents H;
i and j represent 0-2 such that the sum of i and j is 1-3;

B represents

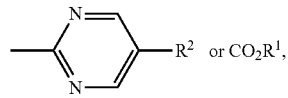

in which R¹ is selected from the group consisting of $C_{1-6}$alkyl and $C_{1-6}$haloalkyl and R² is selected from the group consisting of chloro and bromo, $C_{1-4}$ alkyl, $C_{1-4}$hydroxyalkyl and $C_{1-4}$haloalkyl, in which the halo portion is selected from fluoro, chloro, bromo and iodo.

9. A compound in accordance with claim 1 selected from the group consisting of:

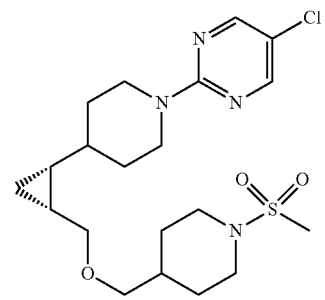

1.1

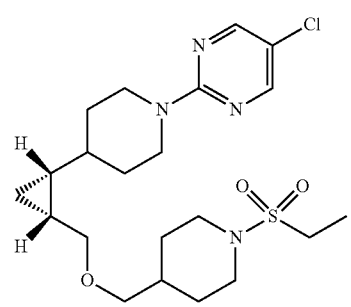

1.2

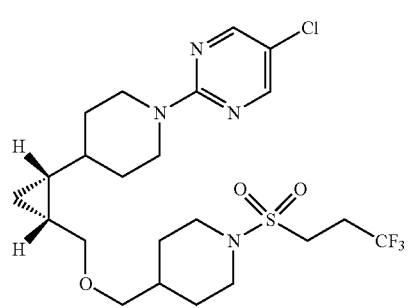

1.3

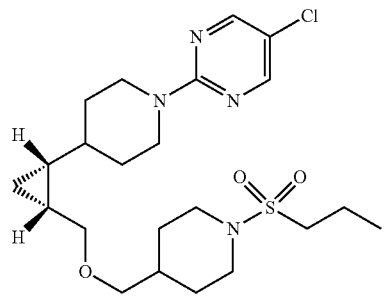

1.4

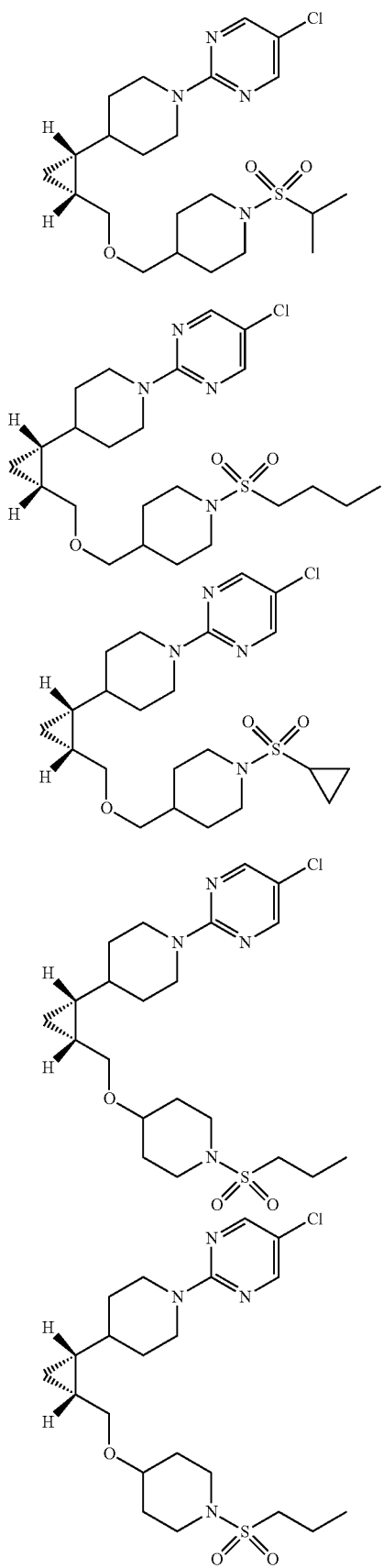
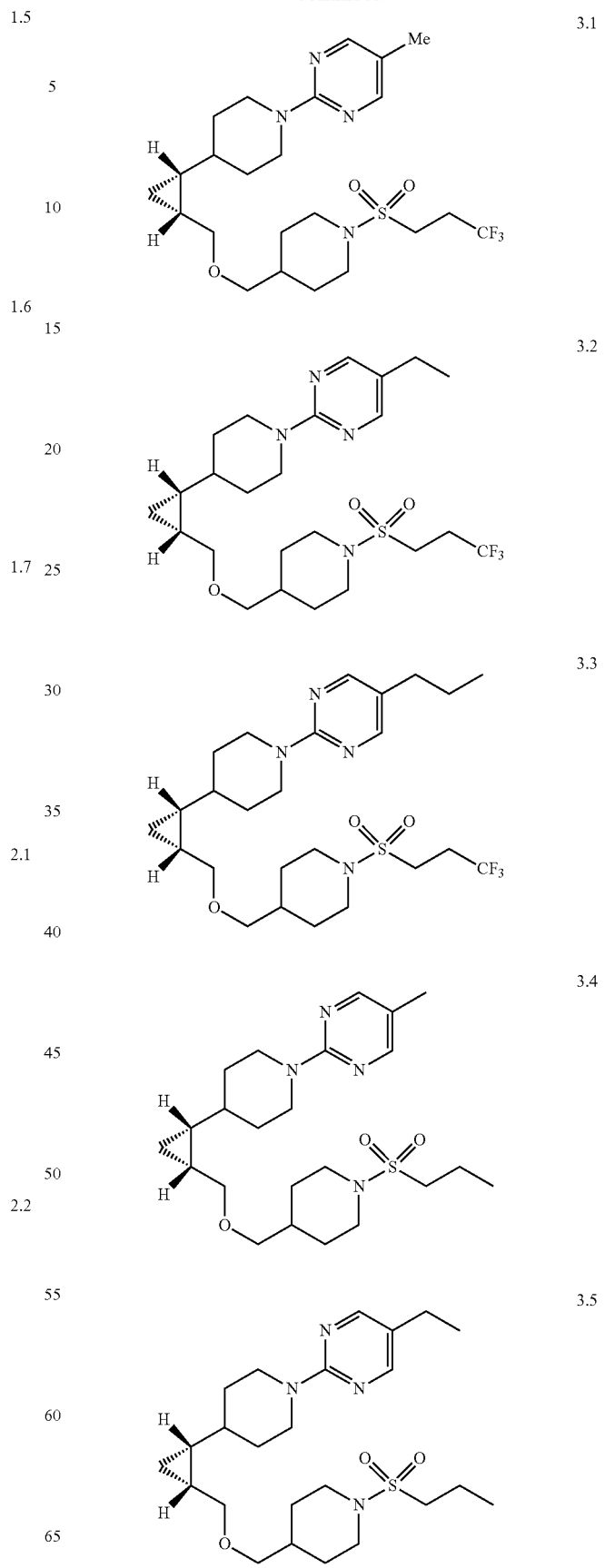

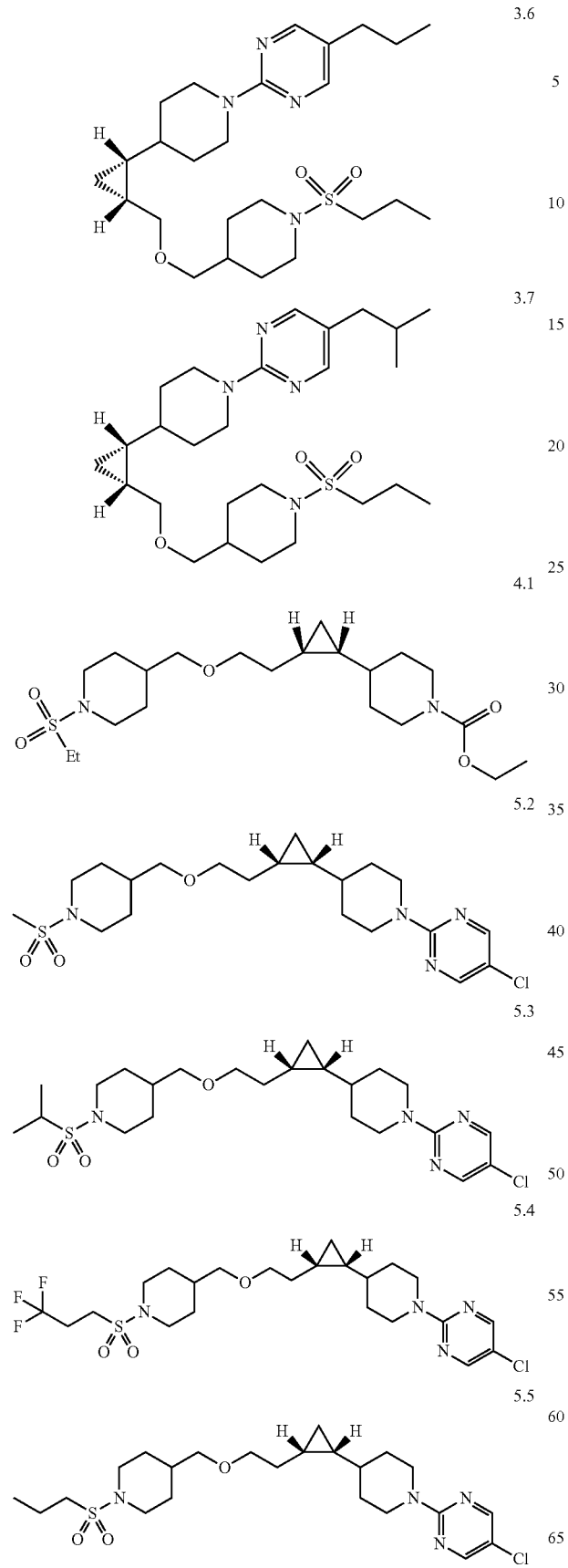
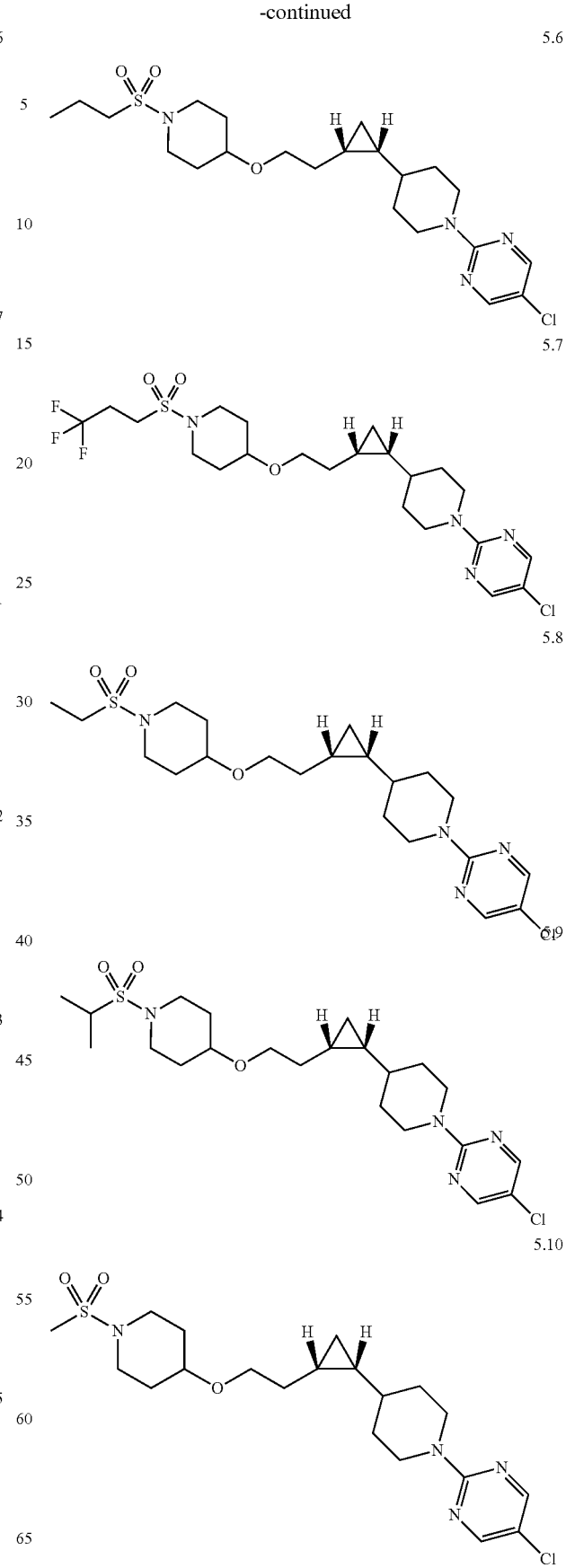

5.11
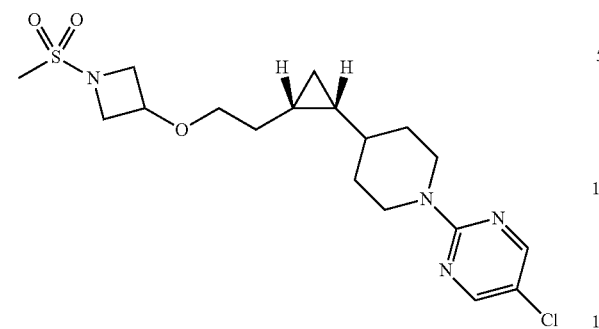
5.12
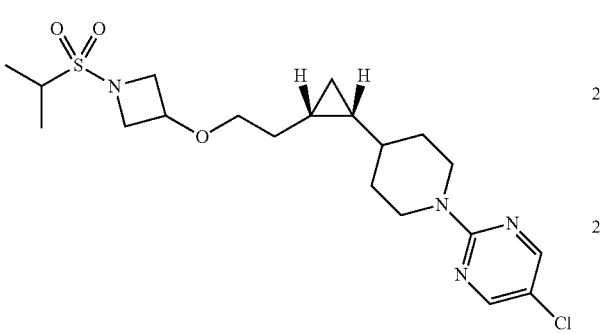
5.13
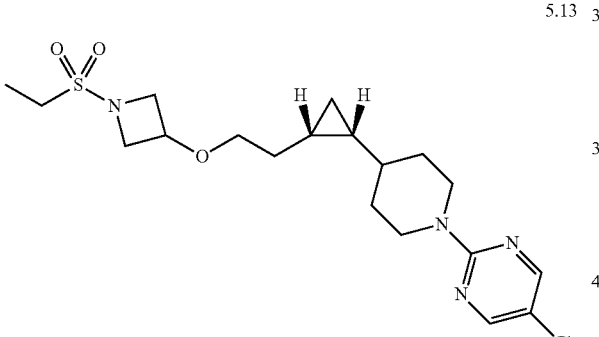
5.14
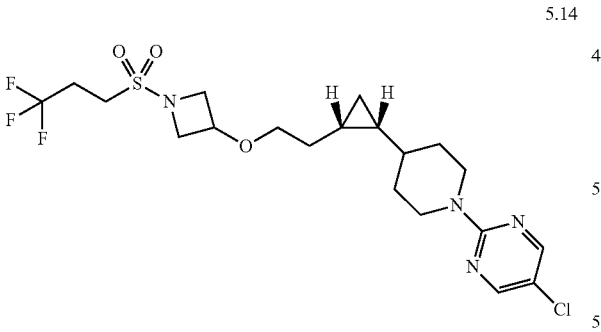
5.15
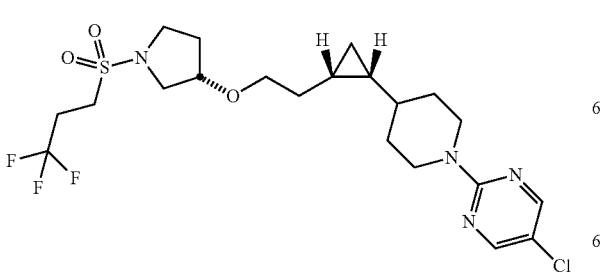
5.16
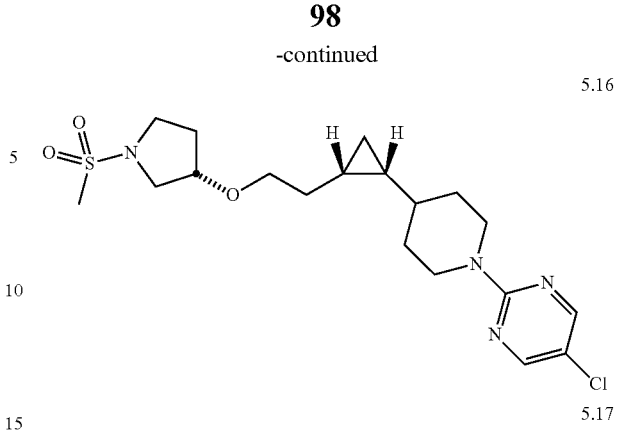
5.17
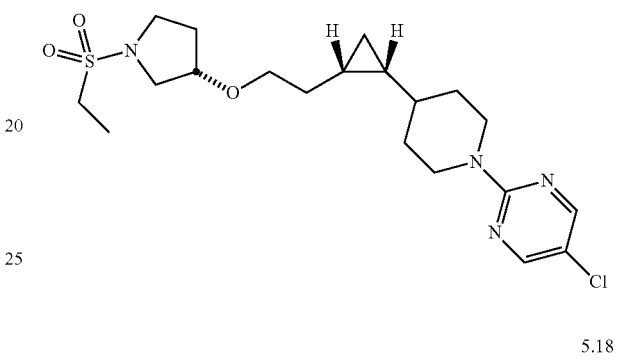
5.18
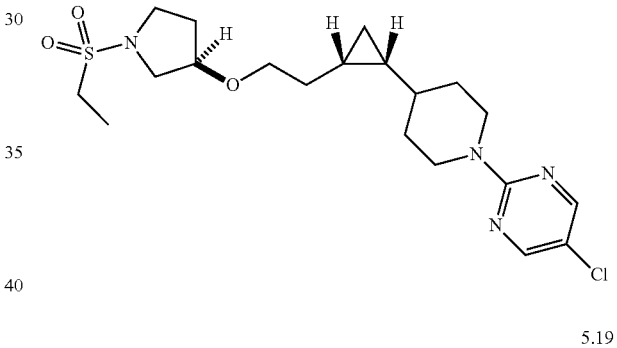
5.19
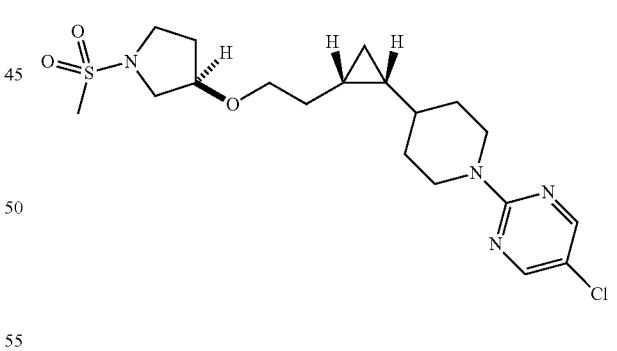
5.20
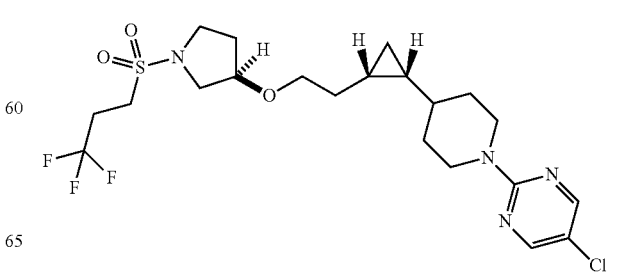

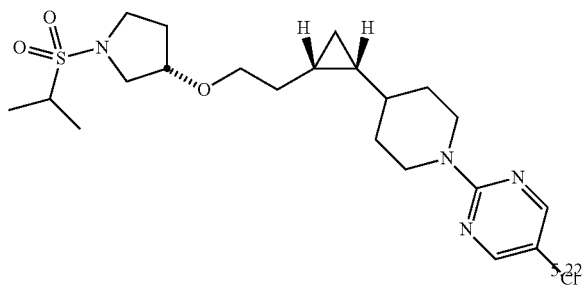

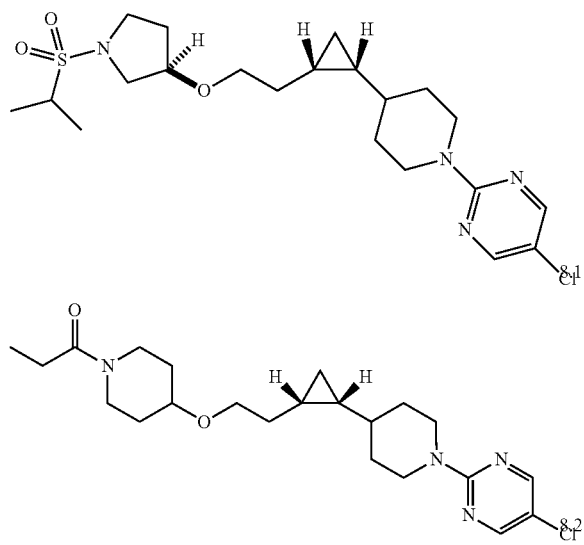

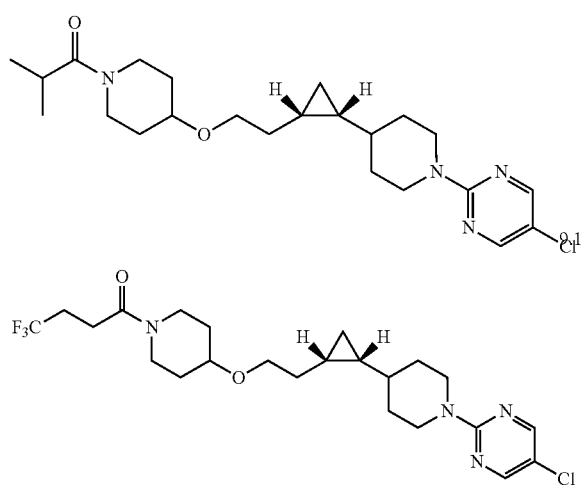

or a pharmaceutically acceptable salt thereof.

10. A pharmaceutical composition comprised of a compound in accordance with claim 1, or a pharmaceutically acceptable salt thereof, in combination with a pharmaceutically acceptable carrier.

11. A method treating type 2 diabetes in a mammalian patient in need of such treatment comprising administering to the patient a compound in accordance with claim 1, or a pharmaceutically acceptable salt thereof, in an amount that is effective to treat type 2 diabetes.

12. A compound which is:

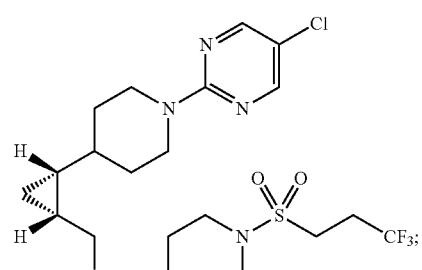

or a pharmaceutically acceptable salt thereof.

13. A compound which is:

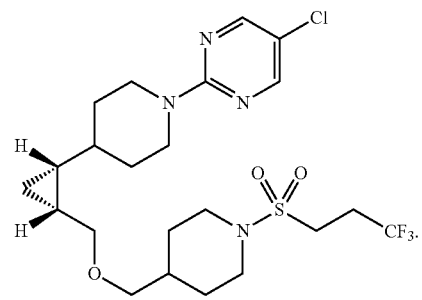

* * * * *